(12) United States Patent
Thompson et al.

(10) Patent No.: US 11,219,434 B2
(45) Date of Patent: *Jan. 11, 2022

(54) METHOD OF SURGICAL DISSECTION AND/OR GUIDANCE OF OTHER MEDICAL DEVICES INTO BODY

(71) Applicant: Medtronic, Inc., Minneapolis, MN (US)

(72) Inventors: Mark Thompson, Minneapolis, MN (US); Darrin Dickerson, Minneapolis, MN (US); Brett S. Bowman, Minneapolis, MN (US); Christopher F. Kelly, Minneapolis, MN (US); William W. Malecki, Minneapolis, MN (US); David Francischelli, Minneapolis, MN (US); Mark Stewart, Minneapolis, MN (US); Thomas Daigle, Minneapolis, MN (US); Douglas Gubbin, Minneapolis, MN (US); David Kim, Minneapolis, MN (US); Paul Rothstein, Minneapolis, MN (US); Adam Podbelski, Minneapolis, MN (US); Christopher Plott, Minneapolis, MN (US); Benjamin K. Yaffe, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 549 days.

This patent is subject to a terminal disclaimer.

(21) Appl. No.: 16/154,928

(22) Filed: Oct. 9, 2018

(65) Prior Publication Data

US 2019/0038270 A1 Feb. 7, 2019

Related U.S. Application Data

(63) Continuation of application No. 11/698,764, filed on Jan. 26, 2007, now Pat. No. 10,098,618.

(Continued)

(51) Int. Cl.
*A61B 17/00* (2006.01)
*A61B 90/30* (2016.01)

(Continued)

(52) U.S. Cl.
CPC ...... *A61B 17/00234* (2013.01); *A61B 1/0055* (2013.01); *A61B 90/30* (2016.02);

(Continued)

(58) Field of Classification Search
CPC ................................................ A61B 2017/003
See application file for complete search history.

(56) References Cited

U.S. PATENT DOCUMENTS 5,174,276 A 12/1992 Crockard
5,575,766 A 11/1996 Swartz et al.
(Continued)

FOREIGN PATENT DOCUMENTS

WO 0189440 11/2001
WO 2005092200 10/2005
(Continued)

OTHER PUBLICATIONS

Wolf, et al., "Video-assisted bilateral pulmonary vein isolation and left atrial appendage exclusion for atrial fibrillation," Journal of Thoracic & Cardiovascular Surgery, vol. 130, No. 3, pp. 797-802 (Sep. 2005).

(Continued)

*Primary Examiner* — Scott Luan
(74) *Attorney, Agent, or Firm* — Dicke, Billig & Czaja, PLLC

(57) ABSTRACT

A method of surgical dissection of tissue with a dissector comprising: an elongate shaft comprising a proximal portion and a distal portion, wherein the distal portion comprises a plurality of segments that articulate with respect to one another and the plurality of segments includes a distal segment having a distal end; and a handle attached to the proximal portion of the shaft, wherein the handle comprises controls for articulating the plurality of segments of the distal portion of the shaft with respect to one another, comprising the steps of: positioning the distal end of the dissector in a body; advancing the distal end through the body to dissect tissue; and simultaneously articulating the plurality of segments with respect to one another. A method of surgical dissection of tissue and guiding a second device to a desired physiological location with a first device.

14 Claims, 34 Drawing Sheets

Related U.S. Application Data

(60) Provisional application No. 60/852,145, filed on Oct. 17, 2006, provisional application No. 60/762,683, filed on Jan. 27, 2006.

(51) Int. Cl.
    *A61B 1/005*     (2006.01)
    *A61B 90/00*     (2016.01)
    *A61B 17/02*     (2006.01)
    *A61B 17/32*     (2006.01)
    *A61B 18/14*     (2006.01)

(52) U.S. Cl.
    CPC ....... *A61B 17/0218* (2013.01); *A61B 18/1482* (2013.01); *A61B 2017/003* (2013.01); *A61B 2017/00367* (2013.01); *A61B 2017/320044* (2013.01); *A61B 2090/0811* (2016.02)

(56) References Cited

U.S. PATENT DOCUMENTS

| | | | |
|---|---|---|---|
| 5,649,957 A | 7/1997 | Levin | |
| 5,704,898 A | 1/1998 | Kokish | |
| 5,738,628 A | 4/1998 | Sierocuk et al. | |
| 5,913,870 A | 6/1999 | DeFonzo et al. | |
| 6,001,120 A | 12/1999 | Levin | |
| 6,142,994 A | 11/2000 | Swanson et al. | |
| 6,248,062 B1 | 6/2001 | Adler et al. | |
| 6,379,319 B1 | 4/2002 | Garibotto et al. | |
| 6,517,550 B1 | 2/2003 | Konya et al. | |
| 6,660,016 B2 | 12/2003 | Lindsay | |
| 6,786,898 B2 | 9/2004 | Guenst | |
| 6,827,715 B2 | 12/2004 | Francischelli et al. | |
| 6,858,005 B2 | 2/2005 | Ohline et al. | |
| 7,122,034 B2 | 10/2006 | Belhe et al. | |
| 7,235,083 B1 | 6/2007 | Perez et al. | |
| 7,803,107 B2 | 9/2010 | Carrillo | |
| 2002/0082595 A1 | 6/2002 | Langberg et al. | |
| 2002/0123698 A1 | 9/2002 | Garibotto et al. | |
| 2002/0138109 A1 | 9/2002 | Keogh et al. | |
| 2003/0144656 A1 | 7/2003 | Ocel et al. | |
| 2004/0106918 A1 | 6/2004 | Cox et al. | |
| 2004/0133189 A1 | 7/2004 | Sakurai | |
| 2004/0138526 A1 | 7/2004 | Guenst | |
| 2004/0225233 A1 | 11/2004 | Frankowski et al. | |
| 2004/0267326 A1 | 12/2004 | Ocel et al. | |
| 2005/0090811 A1 | 4/2005 | Doyle et al. | |
| 2005/0148820 A1 | 7/2005 | Carrillo | |
| 2005/0203561 A1 | 9/2005 | Palmer et al. | |
| 2005/0203562 A1 | 9/2005 | Palmer et al. | |
| 2006/0094932 A1 | 5/2006 | Goldfarb et al. | |
| 2006/0229594 A1 | 10/2006 | Francischelli et al. | |
| 2006/0235372 A1 | 10/2006 | Ward | |
| 2006/0270900 A1 | 11/2006 | Chin et al. | |
| 2007/0135803 A1 | 6/2007 | Belson | |
| 2007/0213687 A1 | 9/2007 | Barlow | |

FOREIGN PATENT DOCUMENTS

| | | |
|---|---|---|
| WO | 2005092201 | 10/2005 |
| WO | 2006073582 | 7/2006 |

OTHER PUBLICATIONS

Saltman, et al., "A Completely Endoscopic Approach to Microwave Ablation for Atrial Fibrillation," The Heart Surbery Forum #2003-11333, (Jan. 2003), pp. E38-E41, found on website: www.hsforum.com/vol6/issue3/2003-11333.html.

Manasse, et al., "A Video-Assisted Thoracoscopic Technique to Encircle the Four Pulmonary Veins: A New Surgical Intervention for Atrial Fibrillation Ablation," The Heart Surgery Forum #2002-01889, (Apr. 2002), pp. 337-339, found on website: www.hsfurum.com/vol5/issue4/2002-10889.html.

Salenger, et al., "The Completely Endoscopic Treatment of Atrial Fibrillation: Report on the First 14 Patients with Early Results," The Heart Surgery Forum #2004-1111, (Nov. 2004), pp. E554-E558, found on website: www.hsforum.com/vol7/issue6/2004-1111.html.

Pruitt, et al., "Totally Endoscopic Ablation of Lone Atrial Fibrillation: Initial Clinical Experience," Ann Thorac Surg 2006;81:1325-1331.

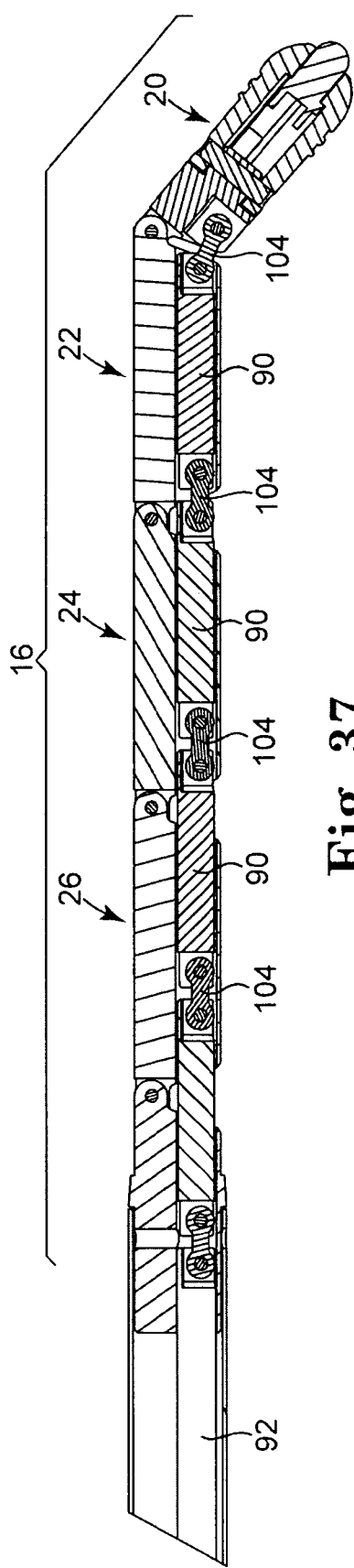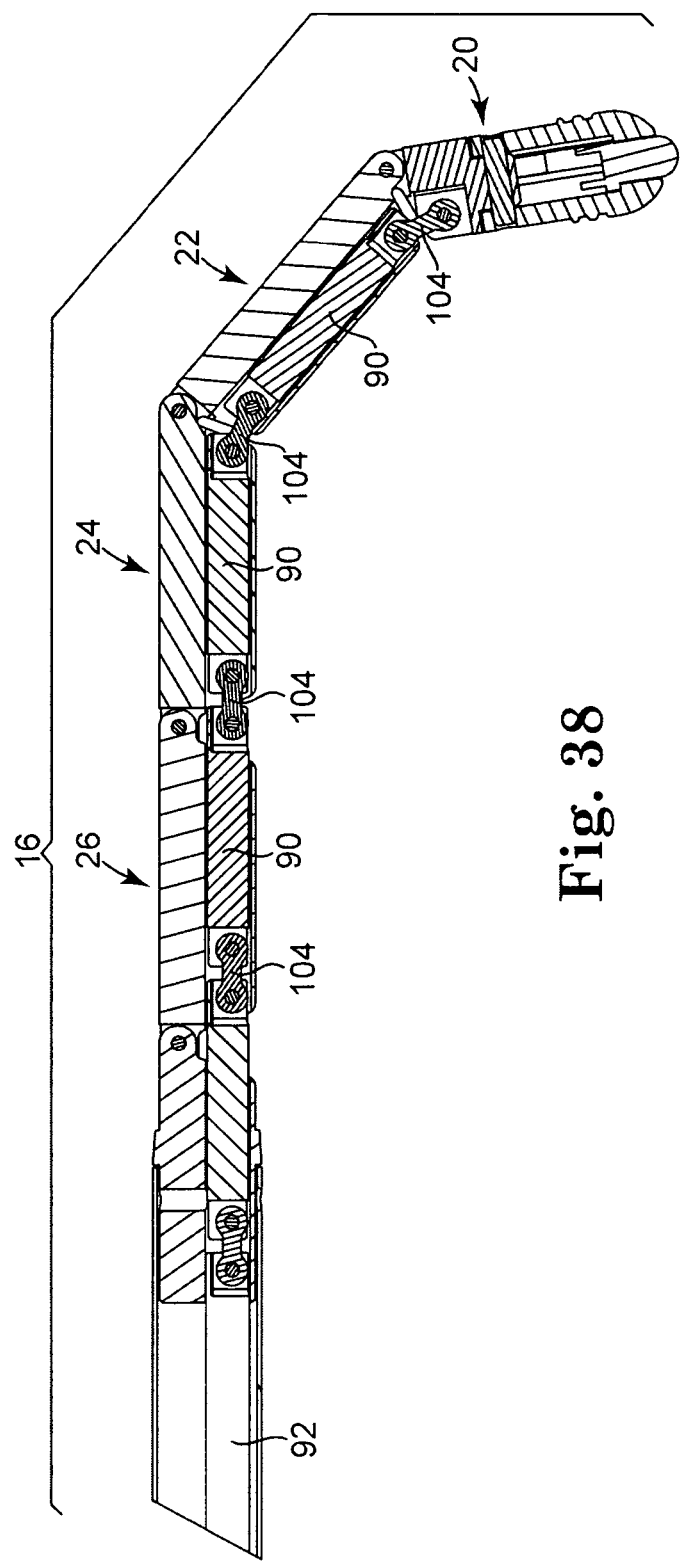

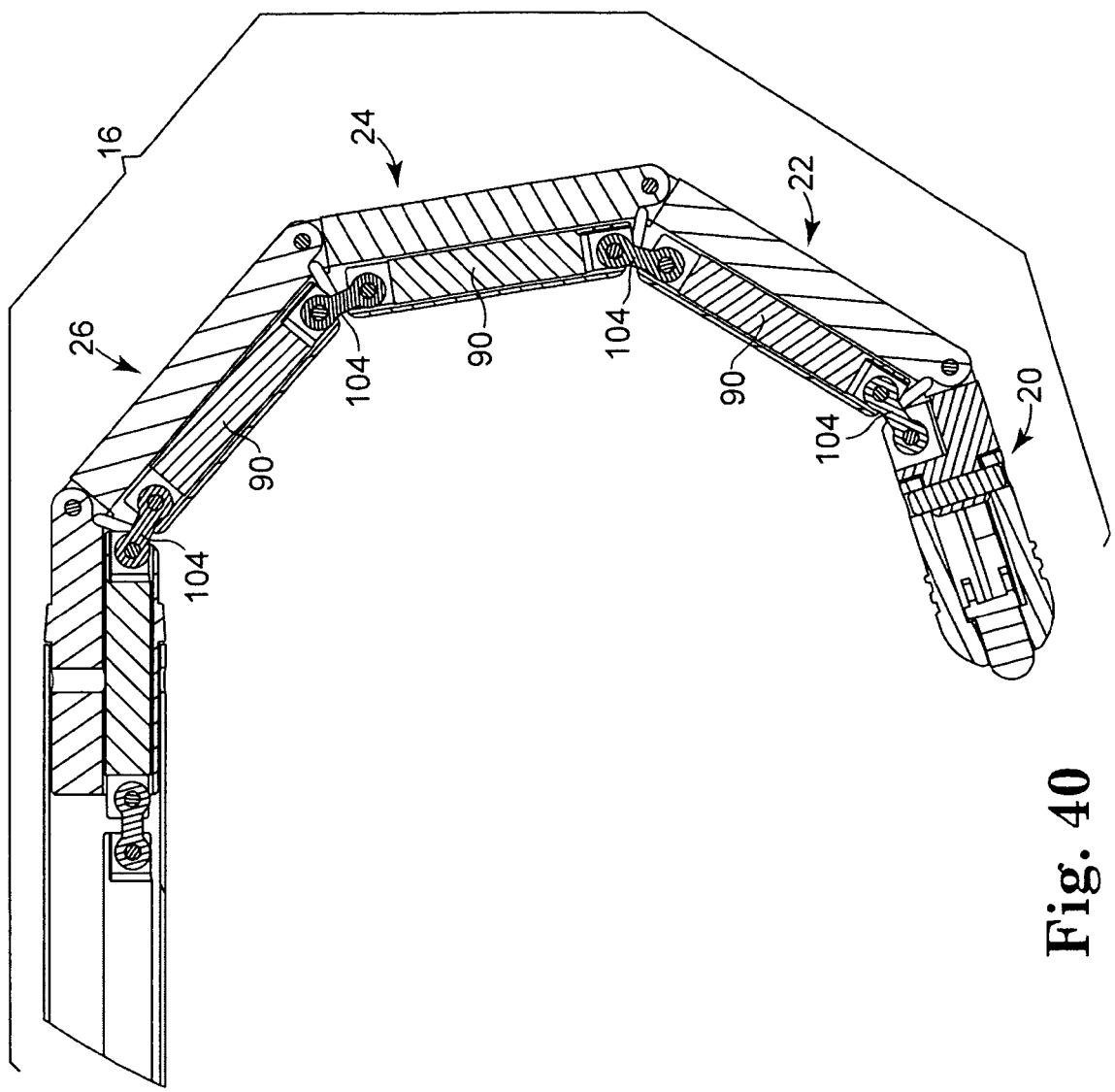

METHOD OF SURGICAL DISSECTION AND/OR GUIDANCE OF OTHER MEDICAL DEVICES INTO BODY

CROSS REFERENCE TO RELATED APPLICATIONS

This application is a continuation of U.S. Patent Application having Ser. No. 11/698,764, filed Jan. 26, 2007, which claims the benefit of both U.S. Provisional Application having Ser. No. 60/762,683, filed Jan. 27, 2006, entitled "MEDICAL DEVICE," and U.S. Provisional Application having Ser. No. 60/852,145, filed Oct. 17, 2006, entitled "MEDICAL DEVICE," which applications are incorporated herein by reference in their entireties.

This application also incorporates by reference in its entirety co-pending U.S. Patent Application having Ser. No. 11/698,807, filed on Jan. 26, 2007, entitled "DEVICE AND SYSTEM FOR SURGICAL DISSECTION AND/OR GUIDANCE OF OTHER MEDICAL DEVICES INTO BODY".

FIELD OF THE INVENTION

The present invention relates generally to a medical device and method for surgical dissection and/or guidance of other medical devices into a body and, in particular, a medical device and method for both dissecting cardiac tissue prior to positioning an ablation device, and guiding the ablation device into a beating heart to perform lesions on the heart during a minimally invasive procedure.

BACKGROUND OF THE INVENTION

Various specialized medical devices, such as ablation devices, cardiac leads, ultrasonic catheters, balloon angioplasty catheters, electrophysiological diagnostic catheters, pressure monitoring catheters, etc., may require the use of a delivery system for deploying the device in a desired internal body space, such as the heart, for example. In addition, in some cases, dissection of tissue is desired or necessary to guide or deliver such specialized medical devices to a desired location.

Although the present invention contemplates devices and systems for dissecting tissue and/or guiding other specialized medical devices to many areas of the body, in particular, the present application will focus on one exemplary desired location and one exemplary specialized medical device. The focus will be primarily on delivery of an ablation device to an area on or near the heart, which, in particular, is around the two separate pairs of pulmonary veins on both sides of the heart. Similarly, the present invention contemplates the use of the present inventive devices and systems to treat various conditions. However, in particular, the present application will focus on treatment for heart arrhythmias (e.g., atrial fibrillation) using ablation procedures.

In a normal heart, contraction and relaxation of the heart muscle (myocardium) takes place in an organized fashion as electrochemical signals pass sequentially through the myocardium from the sinoatrial (SA) node located in the right atrium to the atrialventricular (AV) node and then along a well-defined route which includes the His-Purkinje system into the left and right ventricles. Sometimes abnormal rhythms occur in the atrium which are referred to as atrial arrhythmia. Three of the most common arrhythmias are ectopic atrial tachycardia, atrial fibrillation, and atrial flutter. Arrhythmia can result in significant patient discomfort and even death because of a number of associated problems, including the following: (1) an irregular heart rate, which causes a patient discomfort and anxiety; (2) loss of synchronous atrioventricular contractions, which compromises cardiac hemodynamics resulting in varying levels of congestive heart failure; and (3) stasis of blood flow, which increases vulnerability to thromboembolism. It is sometimes difficult to isolate a specific pathological cause of the arrhythmia, although it is believed that the principal mechanism is one or a multitude of stray circuits within the left and/or right atrium. These circuits or stray electrical signals are believed to interfere with the normal electrochemical signals passing from the SA node to the AV node and into the ventricles.

Treatment of arrhythmias may be accomplished by a variety of approaches, including drugs, surgery, implantable pacemakers/defibrillators, and catheter ablation. While arrhythmic drugs may be the treatment of choice for many patients, these drugs may only mask the symptoms and do not cure the underlying cause. Implantable devices, on the other hand, usually can correct an arrhythmia only after it occurs. Surgical and catheter-based treatments, by contrast, may actually cure the problem usually by ablating the abnormal arrhythmogenic tissue or abnormal pathway responsible for the arrhythmia. The catheter-based treatments rely on the application of various destructive energy sources to the target tissue including direct current energy sources to the target tissue, including direct current electrical energy, radiofrequency electrical energy, microwave energy, laser energy, cryoenergy, ultrasound, and the like.

One surgical method of treating arrhythmia is the "Maze" procedure, which relies on a prescribed pattern of incisions to anatomically create a convoluted path, or maze, for electrical propagation within the left and right atria. The procedure employs incisions in the right and left atria, which divide the atria into electrically isolated portions, and which in turn results in an orderly passage of a depolarization wave front from the SA node to the AV node, while preventing reentrant wave front propagation. The Maze procedure has been effective in curing arrhythmias, but the procedure is technically difficult. The procedure also requires open heart surgery, in which the breastbone is divided and the surgeon has direct access to the heart.

More recently, Maze-like procedures have been developed utilizing ablation catheters that can form lesions on the endocardium to effectively create a maze for electrical conduction in a predetermined path. Typically, the lesions are formed by ablating tissue with an electrode carried by a catheter. Ablative energy, e.g., high intensity focused ultrasound (HIFU) energy, radiofrequency (RF) energy, microwave energy and/or laser energy, applied to the electrode, causes significant physiological effects in the tissue resulting from thermal and/or mechanical changes or effects. By controlling the energy level, the amount of heat generated in the tissue and the degree of tissue damage or change can also be controlled. Ablation uses lower levels of voltage that creates sufficient heat to cause a desired cell damage, but leaves the tissue structure intact so as to effectively block electrical pathways within the tissue. Irrigation of the electrode(s) with saline or other conductive fluid can decrease the interface impedance, cool the tissue, and allow for a greater lesion depth.

A treatment for atrial fibrillation, in particular, includes ablation around the pulmonary veins, which procedure is called pulmonary vein antrum isolation. Almost all the atrial fibrillation signals are believed to come from the four pulmonary veins and move to the atria. Ablation of the area of the atria that connects to the pulmonary veins provides circular scar tissue that blocks impulses firing within the pulmonary veins from moving to the atria, thereby disconnecting the pathway of abnormal rhythm and preventing atrial fibrillation.

Most ablation devices are designed to access the heart via a mid-line sternotomy. More recently, ablation of cardiac tissue can be carried out through a minimally invasive route, such as between the ribs, through a sub-xyphoid incision or via catheter that is introduced through a vein, and into the heart. Such minimally invasive procedures are generally performed off-pump, which means the heart is beating during the procedure. Such procedures accordingly require several ports for medical devices to enter the area of the heart and perform the procedures.

Ablation of a precise location within the heart requires precise placement of an ablation device within or near the heart. Precise positioning of the ablation device is especially difficult because of the physiology of the heart, particularly as such recently developed procedures generally occur off-pump. As discussed earlier, in some cases, dissection of tissue is necessary to guide or deliver specialized medical devices to their desired location in the body. In particular, with regard to pulmonary vein antrum isolation, tissue connecting each pair of pulmonary veins to pericardial reflections is often dissected allowing ablation device placement on and/or around the pulmonary veins.

In general, if prior art devices for dissection are used, and if guidance of a specialized medical device to a location after the dissection is desired, separate devices are used for dissection and for placing the specialized medical device. Prior art devices that allow for both dissection and placement of another device, in particular with regard to ablation devices, require suturing a catheter at or near the end of the device while the end of the device is near the heart. Suturing near a beating heart involves risk of negative consequences.

Thus, there is a need for an improved device that can dissect tissue and guide specialized medical devices to particular locations in the body. In particular, an improved device and method for dissecting cardiac tissue and placement of ablation devices during minimally invasive procedures on a beating heart are desired.

SUMMARY OF THE INVENTION

The present invention relates to dissection of soft tissue during general, ear, nose and throat (ENT), thoracic, urological, and gynecological surgical procedures. The present invention is of particular applicability for use during minimally invasive surgical procedures or endoscopic procedures, such as during procedures on a beating heart involving ablation (e.g., pulmonary vein antrum isolation). The device includes a shaft with an articulating end that is adjusted by controls in a handle. The articulated end helps to navigate soft tissue around anatomic structures. The articulating end preferably comprises a plurality of moveable or articulable segments that help to dissect tissue and move around anatomic structures. Preferably, the articulated end is also illuminated for identification of distal tip location.

The device may be part of a system used to dissect tissue and/or guide a specialized medical device to a location in the body. The device may be inserted into a location in the body, as described above, via a given entry route, for dissection of tissue. While the device is in the location in the body for dissection purposes, the device may also be used with other components of a system to place a second device in the body. In order to place the second device, the system preferably includes a guide wire that may be fed through a lumen in the device and that may be advanced through the device and connected to one end of a guide member, which has two ends, and that is separate from the device. The guide wire may then be retracted back through the device, with the guide member attached, in order to pull the first end of the guide member to a location in the body, and preferably adjacent or near the distal tip of the device. The second end of the guide member may be attached to a second device, such as a specialized medical device (e.g., an ablation device). The device, with guide member attached, may then be removed from the body by withdrawing the device back through the port of entry, thereby pulling the guide member through the same port, and furthermore pulling the second device on the second end of the guide member into the location in the body at or near where the dissection took place.

The present invention provides advantages over prior art devices and methods for dissection of tissue and/or guidance of medical devices into a body. One advantage is that a plurality of articulable segments of a distal end of the device can have different configurations allowing the end of the device to have, for example, a straight configuration for insertion and removal through a port during a minimally invasive surgical procedure and also allowing the end of the device to articulate into controlled curves while inside the body for dissection and placement purposes. Another advantage is that a portion of the device can remain outside of the body so as to indicate both a plane of articulation and an amount of articulation of the articulating end of the device for informing the user of such relevant information. Yet another advantage of the present invention is the presence of an on-off switch for an illumination source on the distal end of the device, which allows the user to control whether or not an illumination source is turned on. Also, an illumination source indicator is preferably located on the handle, which provides the advantage of allowing the user to know whether or not the illumination source is turned on. A still further advantage is that a guide wire may be used, through a lumen in the device, such as in the case of an ablation procedure in particular, to place a device, which avoids suturing inside the body (e.g., near the beating heart in ablation procedures). Also, with regard to ablation procedures in particular, an additional advantage is that the variability of the articulation of the articulating end of the device allows a surgeon some flexibility in the type of surgical approach chosen for a given procedure and patient. For example, in pulmonary antrum isolation procedures, a surgeon may choose to use either a superior or an inferior approach to the procedure using the device and/or system of the present invention.

A first embodiment of the present invention is a method of surgical dissection of tissue with a dissector comprising: an elongate shaft comprising a proximal portion and a distal portion, wherein the distal portion comprises a plurality of segments that articulate with respect to one another and the plurality of segments includes a distal segment having a distal end; and a handle attached to the proximal portion of the shaft, wherein the handle comprises controls for articulating the plurality of segments of the distal portion of the shaft with respect to one another, comprising the steps of: positioning the distal end of the dissector in a body; advancing the distal end through the body to dissect tissue; and simultaneously articulating the plurality of segments with respect to one another. The distal end may include an illumination source, and the method may further comprise a step of visually locating the distal end of the elongate shaft by observing visible energy from the illumination source passing through tissue. The distal end may include an illumination source, and the method may further comprise a step of differentiating tissue by observing visible energy from the illumination source through tissue.

A second embodiment of the present invention is a method of guiding a second device to a desired physiological location with a first device comprising: an elongate shaft comprising a proximal portion and a distal portion, wherein the distal portion comprises a plurality of segments that articulate with respect to one another and the plurality of segments includes a distal segment having a distal end; a handle attached to the proximal portion of the shaft, wherein the handle comprises controls for articulating the plurality of segments of the distal portion of the shaft with respect to one another; and a guide wire lumen having a proximal and a distal end, wherein the guide wire lumen is disposed along at least a portion of the length of the first device and the guide wire lumen has openings at both the proximal and distal ends, comprising the steps of: inserting the first device, distal end first, into a first opening in a body with the plurality of segments of the distal portion in a substantially straight configuration; advancing the distal portion through the body; articulating the plurality of segments with respect to one another to position the distal portion in a desired physiological location; feeding a guide wire, having a proximal and a distal end, into the proximal opening of the guide wire lumen, distal end first, and through the guide wire lumen until the distal end of the guide wire comes out the distal opening of the guide wire lumen in the distal end of the first device; connecting the second device to the distal end of the guide wire; and pulling the guide wire back through the first device and thereby pulling the second device adjacent the distal end of the first device at or near a desired physiological location. The method may further comprise the step of: removing the first device through the first opening. Prior to the step of removing the first device, the distal portion of the first device may be returned to the substantially straight configuration. The method may further comprise the steps of: disconnecting the second device from the guide wire; and removing the first device and the guide wire through the first opening. The second device may have been inserted into the body through a second opening in the body before connecting the second device to the guide wire. The distal end may include an illumination source, and the method may further comprise the step of visually locating the distal end of by observing visible energy from the illumination source passing through tissue. The illumination source may be turned off and on. The first device may further comprise an articulation lock mechanism for maintaining the distal portion of the device in a desired articulated configuration, and further comprising the step of locking the distal portion in the articulated position while the distal portion is in the desired physiological location. The first device may further comprise an articulation lock mechanism for maintaining the distal portion of the device in a desired articulated configuration, and further comprising the steps of: locking the distal portion in the articulated position while the distal portion is in the desired physiological location; and unlocking the distal portion prior to returning the distal portion of the first device to a substantially straight configuration. The first device may further comprise a guide wire lock that can maintain the position of the guide wire in the guide wire lumen. The method may further comprise the step of locking the guide wire in a position in the guide wire lumen after the step of pulling the guide wire back through the first device such that the second device is adjacent the distal end of the first device.

A third embodiment of the present invention is a method of surgical dissection of tissue and guiding a second device to a desired physiological location with a first device comprising: an elongate shaft comprising a proximal portion and a distal portion, wherein the distal portion comprises a plurality of segments that articulate with respect to one another and the plurality of segments includes a distal segment having a distal end; a handle attached to the proximal portion of the shaft, wherein the handle comprises controls for articulating the plurality of segments of the distal portion of the shaft with respect to one another; and a guide wire lumen having a proximal and a distal end, wherein the guide wire lumen is disposed along at least a portion of the length of the first device and the guide wire lumen has openings at both the proximal and distal ends, comprising the steps of: inserting the first device, distal end first, into a first opening in a body with the plurality of segments of the distal portion in a substantially straight configuration; advancing the distal portion through the body to dissect tissue; articulating the plurality of segments with respect to one another to position the distal portion in a desired physiological location; feeding a guide wire, having a proximal and a distal end, into the proximal opening of the guide wire lumen, distal end first, and through the guide wire lumen until the distal end of the guide wire comes out the distal opening of the guide wire lumen in the distal end of the first device; connecting the second device to the distal end of the guide wire; and pulling the guide wire back through the first device and thereby pulling the second device adjacent the distal end of the first device at or near a desired physiological location. The method may further comprise the step of: removing the first device through the first opening. Prior to the step of removing the first device, the distal portion of the first device may be returned to the substantially straight configuration. The method may further comprise the steps of: disconnecting the second device from the guide wire; and removing the first device and the guide wire through the first opening. The second device may be inserted into the body through a second opening in the body before connecting the second device to the guide wire. The distal end may include an illumination source, and the method further comprise the step of visually locating the distal end by observing visible energy from the illumination source passing through tissue. The illumination source may be turned off and on. The desired physiological location may be with the distal portion of the first device around a pair of pulmonary veins, and the second device is an ablation device. The first device may further comprise an articulation lock mechanism for maintaining the distal portion of the device in a desired articulated configuration, and further comprising the step of locking the distal portion in the articulated position while the distal portion is in the desired physiological location. The first device further may further comprise an articulation lock mechanism for maintaining the distal portion of the device in a desired articulated configuration, and further comprising the steps of: locking the distal portion in the articulated position while the distal portion is in the desired physiological location; and unlocking the distal portion prior to returning the distal portion of the first device to the substantially straight configuration. The first device may further comprise a guide wire lock that can maintain the position of the guide wire in the guide wire lumen. The method may further comprise the step of locking the guide wire in a position in the guide wire lumen after the step of pulling the guide wire back through the first device such that the second device is adjacent the distal end of the first device.

BRIEF DESCRIPTION OF THE DRAWINGS

The present invention will be further explained with reference to the appended Figures, wherein like structure is referred to by like numerals throughout the several views, and wherein:

FIG. 37 is a cross-sectional side view of a distal portion of a shaft of an exemplary embodiment of a dissector/guide in accordance with the present invention, showing a distal segment articulated;

FIG. 38 is an illustration as in FIG. 37, showing a subsequent step in a progression of articulation from the distal segment proximally through multiple segments.

FIG. 40 is an illustration as in FIG. 38, showing a subsequent step in a progression of articulation from the distal segment proximally through multiple segments.

DESCRIPTION OF THE PREFERRED EMBODIMENTS

Figure 1:
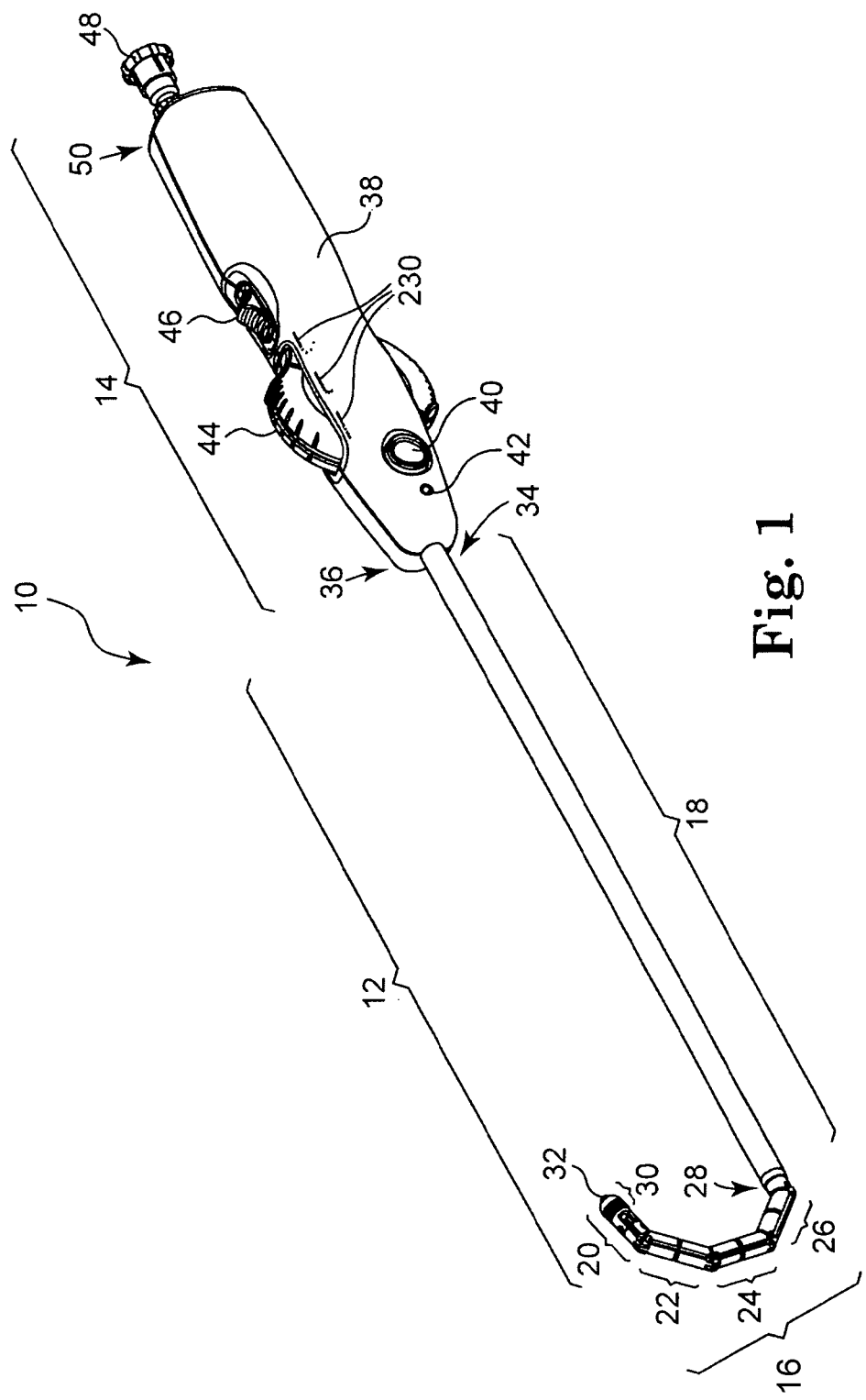
FIG. 1 is a plan view of an exemplary surgical dissector and guide, shown with an articulated distal portion of shaft, in accordance with the present invention.

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

With reference to the accompanying figures, wherein like components are labeled with like numerals throughout the several figures, devices and systems for surgical dissection and guidance of other medical devices, and methods of use thereof, are disclosed, taught and suggested by the multiple embodiments. It is understood that any of the devices and systems described may be used for surgical dissection of and/or guidance of other specialized medical devices to any part of a subject's body including the human body or that of other animals or creatures. In particular, it is contemplated that the devices or systems described are useful during general, ENT, thoracic, urological, and gynecological surgical procedures, although the applicable procedures are not limited to those provided. The devices or systems are useful during minimally invasive surgical procedures, however they may also be useful in open surgical procedures.

The present invention is described below as developed for the application of providing surgical dissection of tissue and guidance of ablation devices, such as for example, in the treatment of arrhythmias of the heart, as described above in the Background section. However, the present invention is not limited to treatment of arrhythmias of the heart. A device contemplated by the present invention preferably includes basic functionality for dissecting tissue in a location in a body and/or guiding another medical device to a location in a body. Such a device preferably includes a manner of changing the shape of a distal portion of the device in order to dissect tissue. Such a device also preferably includes a manner of changing the shape of a distal portion (e.g., curved shape) for positioning the distal portion of the device in a desired anatomical location (e.g., around a blood vessel) in a body. In addition, such a device preferably includes a manner of straightening a distal portion of the device in order to fit though a surgical port. Further, such a device may provide a manner of locking a distal portion in a certain shape or curvature and/or may prevent the distal portion from being straightened once the distal portion has a desired shape. Preferably, shape of a distal portion is controlled from a proximal portion of the device, which may be located outside of the body (i.e., ex vivo) while the distal portion is inside the body. Also preferably, the ex vivo controls for changing the shape of the distal portion of the device may provide an operator with information about the shape of the distal portion while the distal portion is in vivo. Such a device also preferably includes a manner of illuminating the distal portion for purposes of identifying its location, which is relevant for dissection of tissue and/or proper placement of another device. Still further, such a device may be part of a system for guiding another medical device to a location in a body.

With reference initially to FIG. 1, a preferred embodiment of a surgical dissector and guide 10 (hereinafter referred to as "dissector"), in accordance with the present invention, is illustrated having, generally, an elongate shaft 12 and a handle 14. In the case of ablation device procedures, the shaft 12 may be sized and shaped to preferably allow the shaft 12 to be inserted into the thoracic cavity through a trocar port (e.g., 10 mm or 12 mm). However, the device may be differently sized to be inserted through other orifices, such as a small thoracotomy incision, e.g., roughly 1 cm, and/or various other incisions. The shaft 12 comprises a distal portion 16 and a proximal portion 18. The distal portion 16, as seen in FIG. 1, preferably comprises a plurality of segments that are interconnected and articulable. In the FIG. 1 embodiment the distal portion 16 is illustrated as comprising four segments, which include a distal segment 20, and three middle segments 22, 24, 26. The third middle segment 26 is connected to a distal end 28 of the proximal portion 18 of the shaft 12. The distal segment 20 preferably includes a distal tip 30. The distal tip 30 of the shaft 12 may be smooth and convex in shape so as not to cause unintended tissue damage when the distal tip 30 is manipulated through tissue. The distal tip 30 preferably also includes an illumination source 32. A proximal end 34 of the proximal portion 18 is preferably rigidly retained by or attached to the handle 14 at the distal end 36 of the handle 14.

The purpose of the illumination source 32 (e.g., a light) may be to allow visualization of the location and placement of the distal portion 16 within a body. The illumination source 32 may provide sufficient illumination to visualize tissue and confirm the placement of the distal portion 16 of the shaft 12 of the dissector 10. Preferably, the illumination source 32 comprises an LED. Depending on any particular application, other illumination or light sources are also contemplated. The illumination source 32 may provide directional, non-diffuse light, e.g., white in color, with a divergent beam including angle of less than about 45 degrees. The illumination source 32 may, according to a preferred embodiment, provide a light intensity that allows desired illumination of pericardial tissue, for example, with a measurable range of preferably about 5 to 30 foot-candles. However, a larger range of illumination is also contemplated by the present invention, which may be from about 1 to 1,000 foot candles. Preferably, the illumination source 32 will not generate sufficient heat to raise the distal tip 30 and surrounding tissue to greater than about 41° C. for use in heart tissue, in particular.

The handle 14 of the dissector 10 shown in FIG. 1 provides a handheld housing for components that may control the functions of the dissector 10, such as for articulation of the distal portion 16 and illumination of the illumination source 32. The handle 14 shown in FIG. 1 comprises a housing 38, an illumination source on/off switch 40 (the switch 40 may allow the illumination source 32 to be turned on and off during a procedure), an illumination source indicator light 42, a control wheel 44, a lock switch 46, and a guide wire lock 48 on the proximal end 50 of the handle 14. The handle 14 may be designed to be used by an operator in their right or left hand.

As discussed above, generally, the dissector 10 comprises an elongate shaft 12 attached to a handle 14, with the shaft 12 comprising distal 16 and proximal 18 portions. In particular, the distal portion 16 of the shaft 12 will be discussed in more detail. The distal portion 16 preferably changes shape in order to dissect tissue and/or to be positioned in a desired anatomical location. Also, the distal portion 16 preferably may also have a substantially straight configuration in order for the distal portion 16 to fit through a surgical port.

FIG. 1 illustrates the distal portion 16 with segments 20, 22, 24, 26 articulated with respect to one another, and with respect to the proximal portion 18. The purposes of such articulation or movement may include, but not be limited to, to help steer the end of the dissector 10 around anatomical structures, to help dissect tissue, and to help position the illumination source 32 behind and around the anatomic structures of a beating heart, for example, with the handle 14 ex vivo. Different amounts of selective and controlled articulation or movement of the distal portion 16 by a user are possible, thereby allowing the distal portion 16 to accommodate patients that vary in size and anatomic structures. Also, different embodiments of the distal portion 16 of the shaft 12 are contemplated by the present invention, including, for example, embodiments including more or less numbers of segments, using segments of different lengths and sizes together or as similar variations and different attachment means between such segments providing any degree of segment-to-segment or segment-to-portion 18 articulation, such that the distal portion 16 is able to articulate from a substantially straight configuration to arcuate shapes of various configurations and degrees of curvature and vice versa. An arcuate shape or curve may have constant radius or changing radius as controlled at least in part by the connection between segments and proximal portion 18 as to be understood from the description of those components below.

Figure 2:
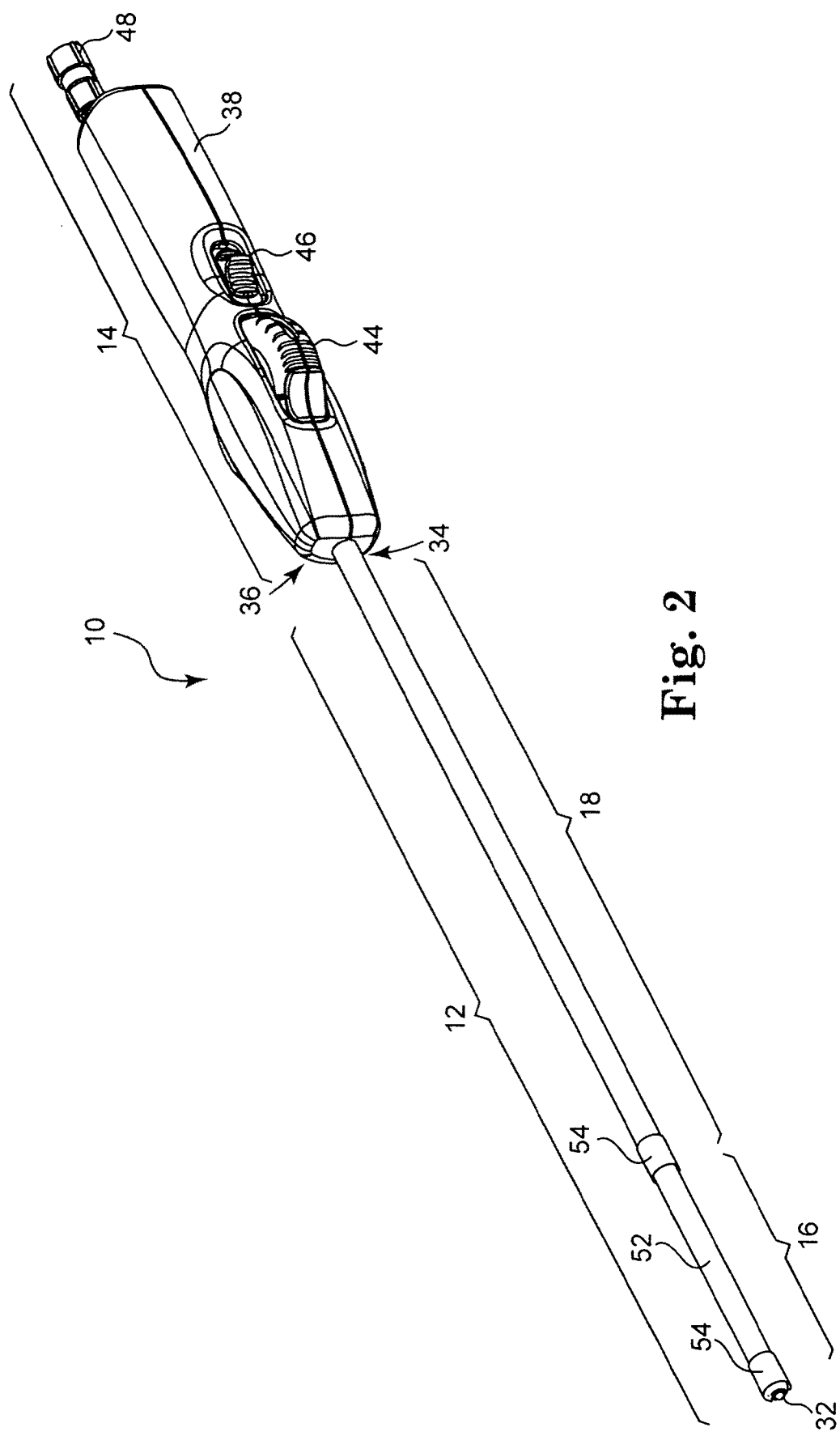
FIG. 2 is a plan view of an exemplary surgical dissector and guide, shown laying on side and with a substantially straight distal portion of shaft, in accordance with the present invention.

FIG. 2 illustrates another possible shape or configuration of the distal portion 16, which is with the segments 20, 22, 24 and 26 (not shown, but covered with sheath) arranged as a substantially straight configuration or shape. A purpose of such a substantially straight shape is to allow the shaft 12 to be both easily inserted into and easily withdrawn from a body through a port having a small diameter, such as a 10 mm trocar port or a 12 mm trocar port, as examples.

Figure 3:
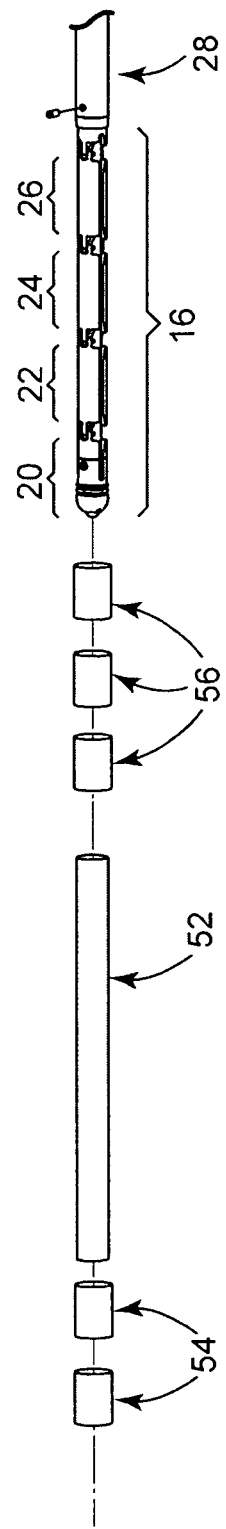
FIG. 3 is a side view of an exemplary distal portion of a shaft of a surgical dissector and guide, shown with a sheath, bands and sheath coverings removed, in accordance with the present invention.
Figure 4:
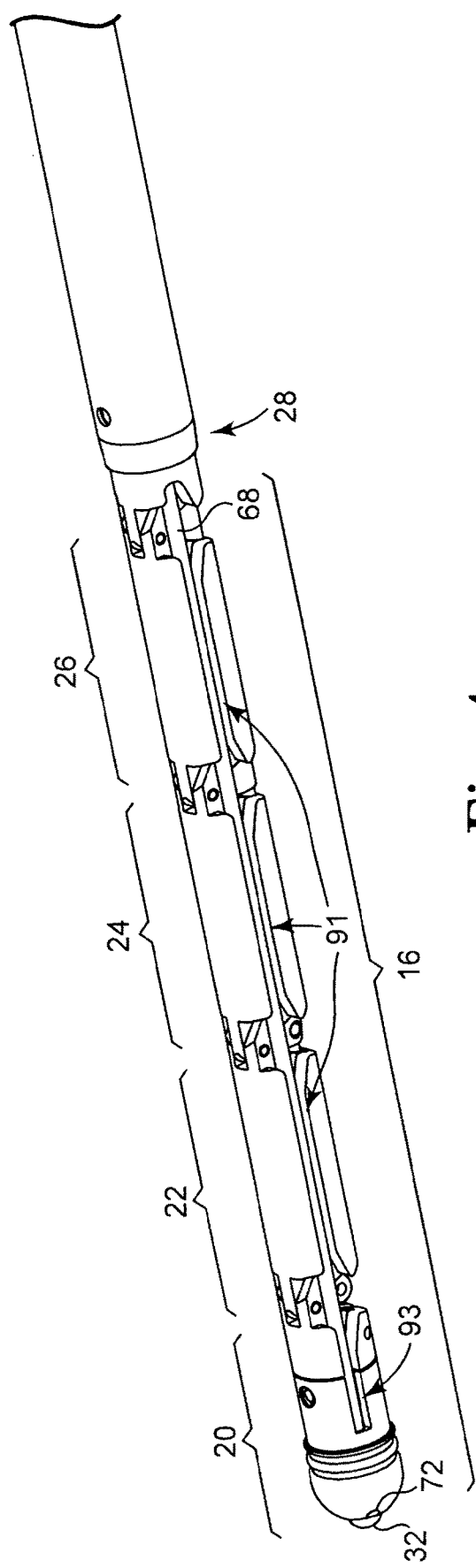
FIG. 4 is a plan view of an exemplary distal portion of a shaft of a surgical dissector and guide, shown without a sheath, bands and sheath coverings, in accordance with the present invention.

In order to help prevent the components of the distal portion 16 of the shaft 12 from inadvertently catching on tissue or compressing tissue while the device is inserted into or during use within a body, the distal portion 16 (and possibly also a portion of the proximal portion 18) of the dissector 10 may be preferably covered with a sheath 52 comprising a flexible material, such as silicone, for example (although other materials are also contemplated). Any material that is flexible or has an elasticity to permit the degree of articulation of the segments, and that is suitable for a given application, is contemplated. FIGS. 2-4 illustrate embodiments that include such a sheath 52. In order to hold the sheath 52 in place on the shaft 12, the ends of the sheath 52 are illustrated as preferably covered with bands 54 preferably comprising a heat shrinkable material that is heat shrunk around the ends of the sheath 52. A suitable band material comprises a heat shrinkable polyester, although other materials are also contemplated by the present invention as may be suitable for different applications.

FIG. 3 shows the distal portion 16 of the shaft 12 with the sheath 52 and bands 54 disassembled from the distal portion 16 of the shaft 12. In addition, FIG. 3 includes three segment coverings 56 that preferably comprise a heat shrinkable material (e.g., like that comprising the bands 54). The segment coverings 56 cover each of the three middle segments 22, 24, and 26, and are located over the segments 22, 24, 26 and under the sheath 52. The purpose of the segment coverings 56 is to hold certain components of the distal portion 16, which run through the three segments 22, 24, 26, together (which will be discussed in more detail below).

Figure 5:
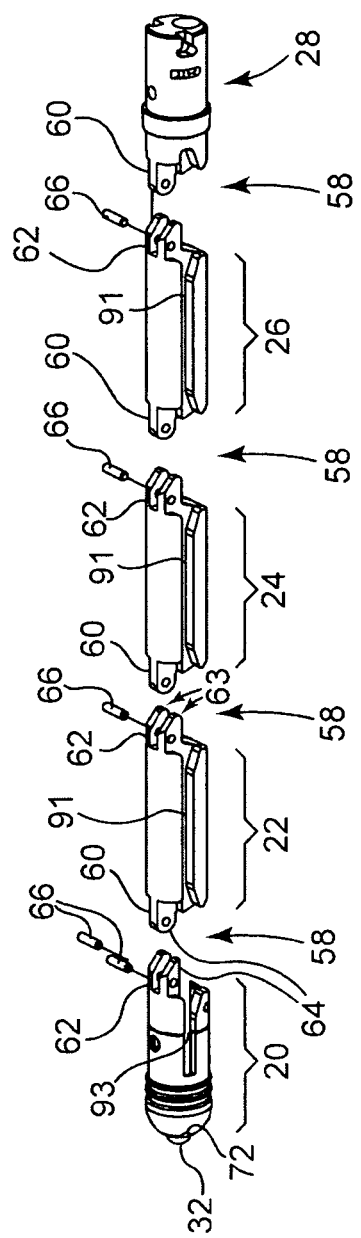
FIG. 5 is an exploded view of the exemplary distal portion of FIG. 4.

FIG. 4 shows a distal portion 16 of an exemplary shaft 12, in accordance with the present invention, shown with a sheath 52, bands 54 or segment coverings 56 removed, as the segments 20, 22, 24, 26 may be provided. FIG. 5 shows the distal portion 16 of FIG. 4 in an exploded view.

In order to allow the segments of the distal portion 16 to articulate with respect to one another and with respect to the proximal portion 18 of shaft 12, articulating connection joints are provided between the segments. In particular, tongue and groove joints 58 are shown in FIG. 5 as pivotally connecting the segments 20, 22, 24, 26 and segment 26 to the distal end 28 of the proximal portion 18 of the shaft 12. Although tongue and groove joints 58 are shown in FIG. 5, other articulating connection joints as known or developed in the future may instead be used that allow for movement and/or articulation of the segments with respect to one another, and as such are also contemplated by the present invention. For example, another possible articulating connection joint that may be used in the present invention is a ball and planar, socket-like joint that is kept under tension. Other such suitable articulating connection joints are also contemplated.

The tongue and groove joints 58 comprise: tongue portions 60 on the distal ends of the respective segments 22, 24, 26 and the distal end 28 of the proximal portion 18 of the shaft 12; and, groove portions 62 on the proximal ends of the segments 20, 22, 24, 26 provided by spaced elements 63. Holes 64 are preferably provided through the tongue portions 60 and the elements 63 of groove portions 62 which may be aligned to be coaxial such that pins 66 inserted through the holes 64 may pivotally attach or connect the tongue 60 and groove 62 portions of the joints 58. Such joints 58 are preferably integrally made with segments but could be otherwise provided. As shown, such tongue and groove joints 58 provide a sufficient degree of rotation between adjacent components to permit controlled shaping of the distal portion 16, in accordance with the present invention. Such degree of rotation can be otherwise limited or enhanced to a greater degree by modifying design features of the tongues and grooves or by substituting other contemplated articulating connection joints.

The elongate shaft 12 of the dissector 10 comprises the distal portion 16 as well as the proximal portion 18. More detail of the articulating distal portion 16 and components that extend through the proximal portion 18 to the handle 14 is given below. A purpose of the proximal portion 18 is to provide a shaft through which components may extend between the distal portion 16 and the handle 14. Another purpose of the proximal portion 18 is to lengthen the shaft 12 so that the articulating distal portion 16 may reach farther into a body with the handle being ex vivo.

Figure 6:
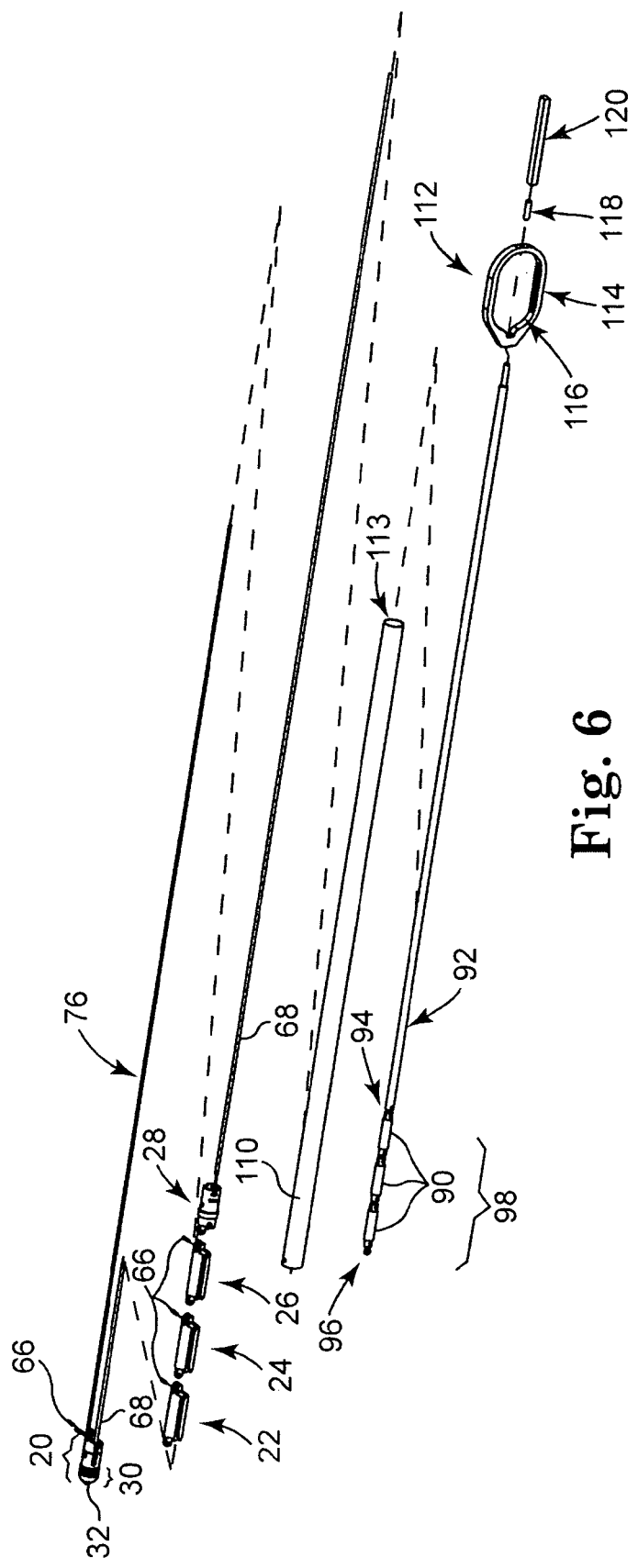
FIG. 6 is an exploded view of components of an exemplary surgical dissector and guide, in accordance with the present invention, that comprise or may be attached to shaft of the exemplary dissector and guide.
Figure 10:
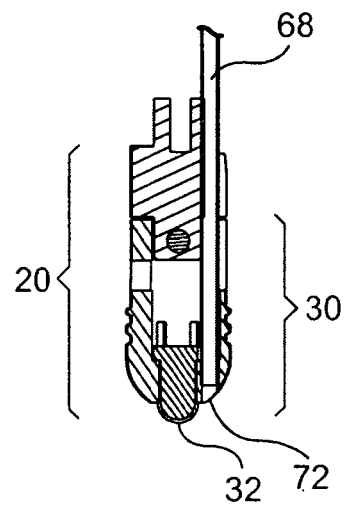
FIG. 10 is a cross-sectional view of the distal segment of FIG. 9 taken along the line 10-10 of FIG. 9.

FIG. 6 shows an exploded view of the shaft 12 and components that extend through the shaft 12 and into or through the handle 14 (some components not shown in previous Figs.). Beginning at the most distal segment 20, the embodiment in FIG. 6 shows a flexible guide wire tube 68 that fits within an opening 72 in the end of the distal tip 30 of the distal segment 20 (not shown in FIG. 6, but can be seen in FIG. 10 as 72) and that extends through groove 91 (as seen in FIG. 5), defined cumulatively as running lengthwise through the segments 22, 24, 26, and the proximal portion 18 of the shaft 12, as assembled in series. Preferably, each of the segments 20, 22, 24, 26 (and any number of more or less segments) includes (as seen in FIG. 4) a groove 91 along and open to the outside of each segment 20, 22, 24, 26, creating an opening for access and containing internally passing elements, such as the guide wire tube 68 and electrical wires 76 as described below. Distal segment 20 preferably has such a groove 93 that only partially extends along its surface to facilitate tube 68 to the opening 72, as shown in FIGS. 4 and 10. The middle segments 22, 24, 26 preferably have such a groove 91 that extends over the respective lengths thereof with proximal most middle segment receiving elements like tube 68 from an internal passage (not shown) of such proximal portion 18, while internal passage is preferably defined entirely through the shaft portion 18 to facilitate passage of the guide wire tube 68 extending to the distal tip 30. Discussion relating to later figures illustrating the handle 14 will describe how the guide wire tube 68 extends through the handle 14.

Another groove 111, like groove 91 for the guide wire tube 68, is also preferably located open and to the outside of the segments 22, 24, 26 of distal portion 16, and preferably contains the electrical wires 76. A portion of the groove 111 can be seen in FIG. 13, discussed below. The discussion above with regard to the groove 91 for the guide wire tube 68 also preferably applies to the groove 111 for the electrical wires 76.

The guide wire tube 68 preferably comprises a coiled wire tube made of 304 stainless steel (SS). The purpose of the guide wire tube 68 is to provide a lumen in which a guide wire may be retained or passed through the dissector 10. The guide wire tube 68 preferably comprises a flexible material or has a design that provides flexibility such that the guide wire tube 68 is able to articulate or move with the segments of the distal portion 16 of the shaft 12 without closing off the lumen inside the tube 68 or restricting movement of a guide wire retained in the tube 68. Any other materials or designs that may provide such a flexible tube are also contemplated by the present invention.

In order to provide power to the illumination source 32 in the distal tip 30, preferably two electrical wires 76 connect the illumination source 32 in the distal tip 30 of the distal segment 20 to a power source, which is preferably located in the handle 14. FIG. 6 shows that the electrical wires 78 extend from the distal tip 30 (i.e., LED housing), through the grooves 111 in each respective segment (and through a groove in the distal segment 20, which is not seen in any figures), and through the proximal portion 18 of the shaft 12 to the handle 14. Discussion relating to later figures illustrating the handle 14 will describe how the electrical wires 76 are connected to a power source in the handle 14.

Figure 7:
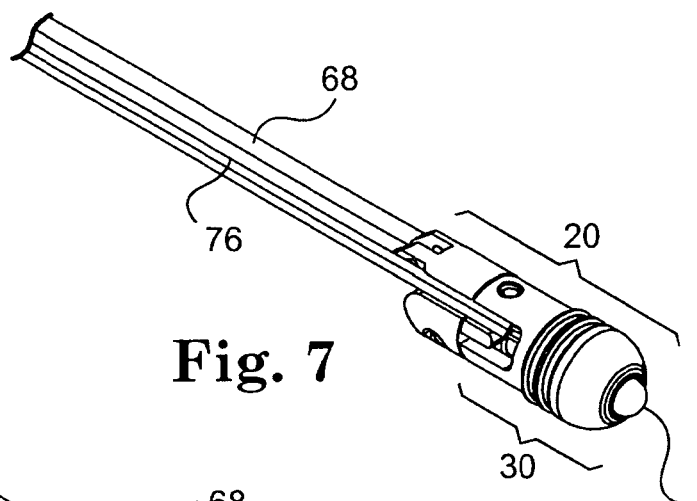
FIG. 7 is a plan view of an exemplary distal segment, in accordance with the present invention, shown with guide wire tube and electrical wires attached.
Figure 8:
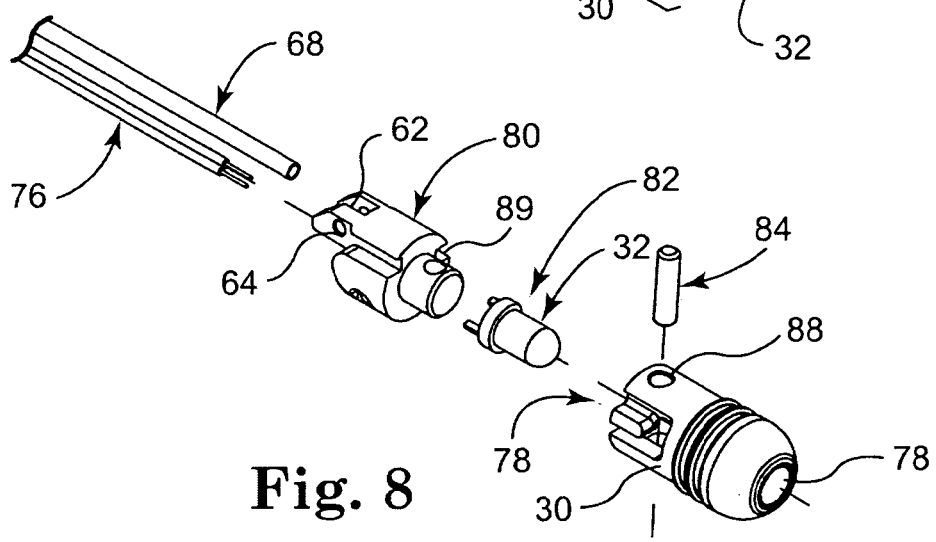
FIG. 8 is an exploded view of the exemplary distal segment of FIG. 7.
Figure 9:
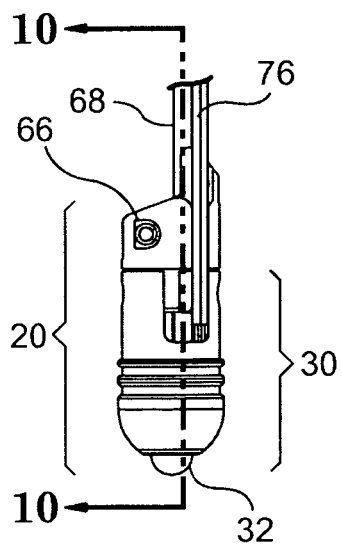
FIG. 9 is a side view of the exemplary distal segment of FIG. 7.

More detail of the distal segment 20 as comprising the distal tip 30 and a recessed portion 80, and how other components extend there from, can be seen in FIGS. 7-10. FIG. 7 shows the distal segment 20 assembled with guide wire tube 68 and electrical wires 76 connected. FIG. 8 is an exploded view of FIG. 7. FIG. 9 is a side view of the distal segment of FIG. 7, and FIG. 10 is a cross section of FIG. 9. Together, FIGS. 7-10 illustrate that the illumination source 32 is preferably placed in a cavity 78 in the distal tip 30 that is open at the tip for the illumination source 32 to pass through. A proximal side of the distal tip 30 fits over and connects to the distal end of the recessed portion 80 of the distal segment 20. The guide wire tube 68 is shown extending through groove 93 of the recessed portion 80 and the distal tip 30. The electrical wires 76 are shown preferably soldered to the lead end 82 of the illumination source 32. A pin 84 holds illumination source 32 in place by extending through coaxially aligned holes 86, 88 located on the recessed portion 80 of the distal segment 20 and the distal tip 30, respectively, and by retaining the illumination source 32 between the recessed portion 80 and distal tip 30.

Figure 11:
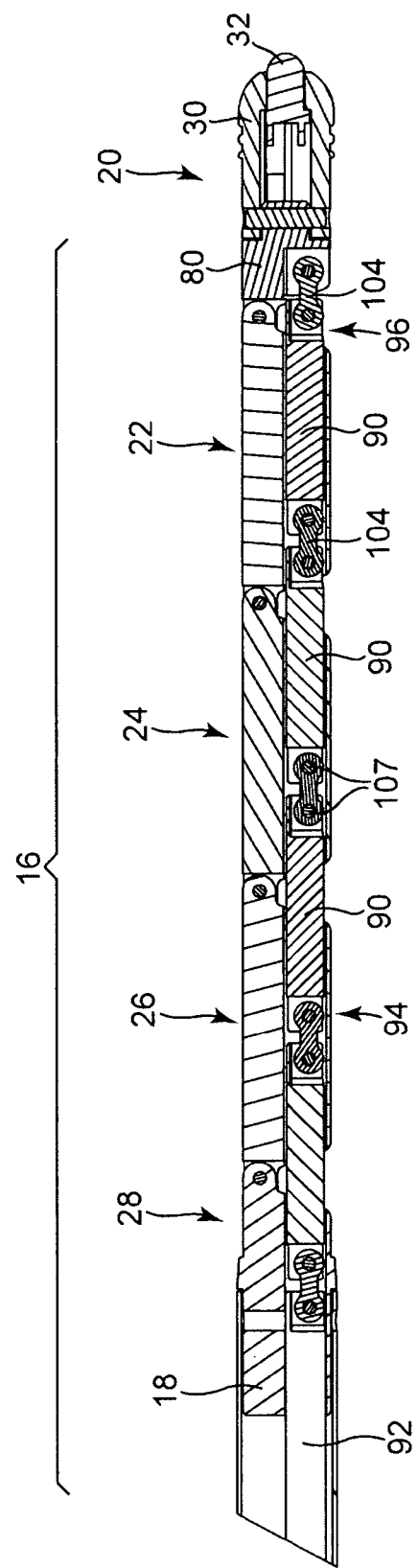
FIG. 11 is a cross-sectional view of a distal portion of a shaft (and some of proximal portion), in accordance with the present invention, showing the piston assembly.

In order to cause controlled articulation of the segments of the distal portion 16 with respect to one another, a piston assembly 98 (FIG. 6) is preferably disposed within the distal portion 16 and connected proximally to a push/pull rod 92 that extends through the proximal portion 18 and into the handle 14, where controls (which will be discussed later) are present to push or pull the rod 92 which straightens or articulates the pistons and segments. Referring back to FIG. 6, the figure shows a set of three pistons 90, that are part of the piston assembly 98, and that are lined up end-to-end and pivotally connected. The pistons 90 are also attached to a push/pull rod 92 at the proximal end 94 of the set of pistons 90. The piston assembly 98 is also preferably disposed within pistons lumens (one of which shown in FIG. 13 as 109) through the segments 22, 24, 26, as shown in FIG. 11. FIG. 11 shows that the pistons 90 are pivotally connected and extend lengthwise through (one each) the three middle segments 22, 24, 26 of the distal portion 16 of the shaft 12. Each of the three pistons 90 is generally slidably disposed within a respective one of the three middle segments 22, 24, 26. The distal end 96 of the piston assembly 98 is preferably pivotally connected to the recessed portion 80 of the distal segment 20, and the proximal end 94 is pivotally connected to the push/pull rod 92.

Figure 12:
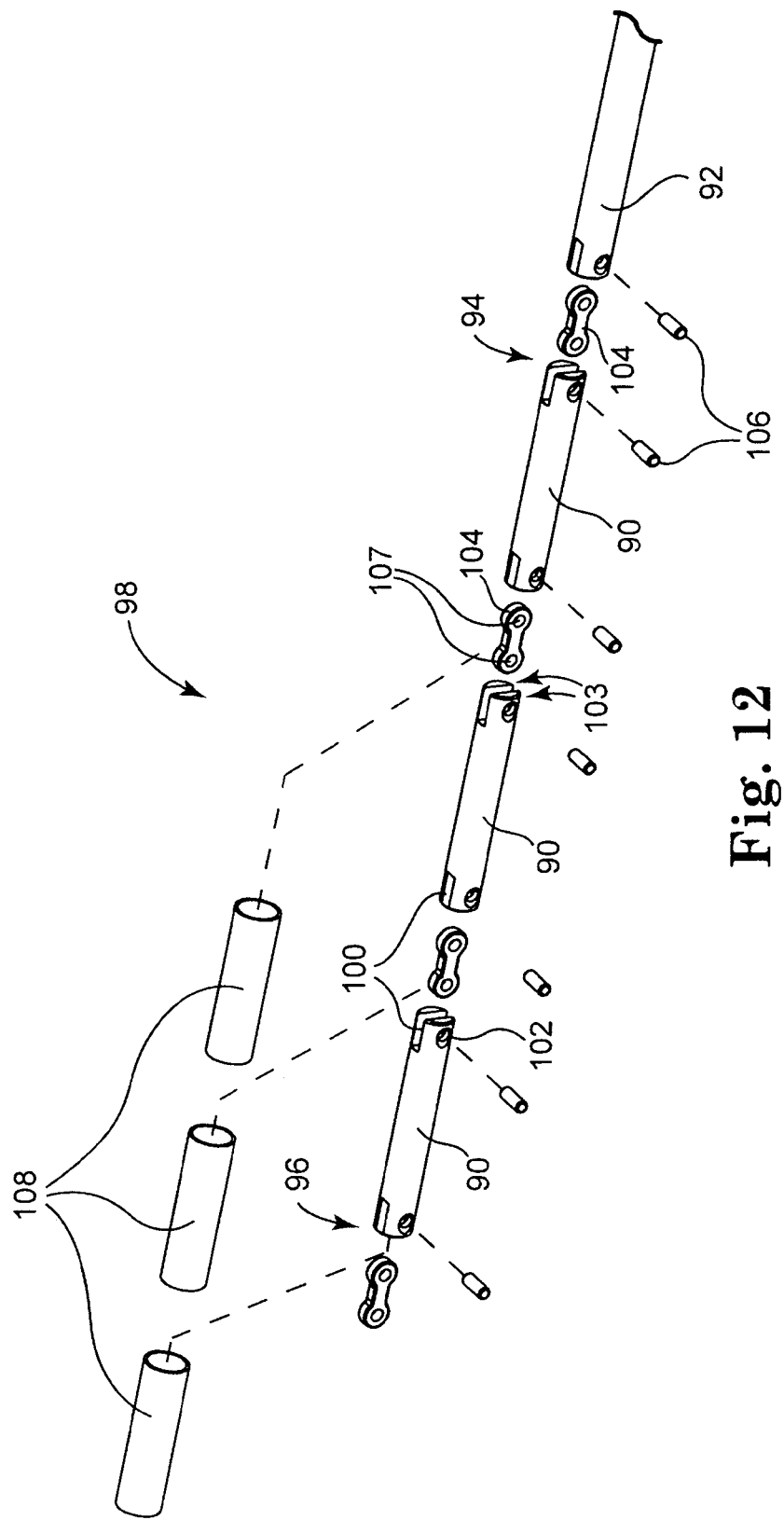
FIG. 12 is an exploded view of an exemplary piston assembly, in accordance with the present invention.

In order to allow the pistons 90 of the piston assembly 98 to articulate with respect to one another and with respect to the distal segment 20 and push/pull rod 92, articulating connection joints are provided between the components. In particular, FIG. 12 illustrates joints comprising grooves 100 and links 104 connected by pins 106. Articulating connection joints, other than those shown in FIG. 12, that allow for movement and/or articulation of the pistons 90 with respect to one another and the other components, could be used and are also contemplated by the present invention. FIG. 12 shows that on both the proximal and distal ends of the pistons 90 there is a groove 100 with two coaxially aligned holes 102 on spaced elements 103. The pistons 90 are preferably connected together, to the recessed portion 80 of the distal segment 20, and to the push/pull rod 92, using links 104 including two holes 107, which are connected to the pistons 90 (and other applicable components) by inserting pins 106 through coaxially aligned holes 102, 107 through the elements 103 and links 104, respectively. The articulating connection joints described provide a sufficient degree of rotation between adjacent components to permit controlled shaping of the distal portion 16, in accordance with the present invention. Such degree of rotation can be otherwise limited or enhanced to a greater degree by modifying the design features of the described joints or by substituting other contemplated articulating joints.

Figure 13:
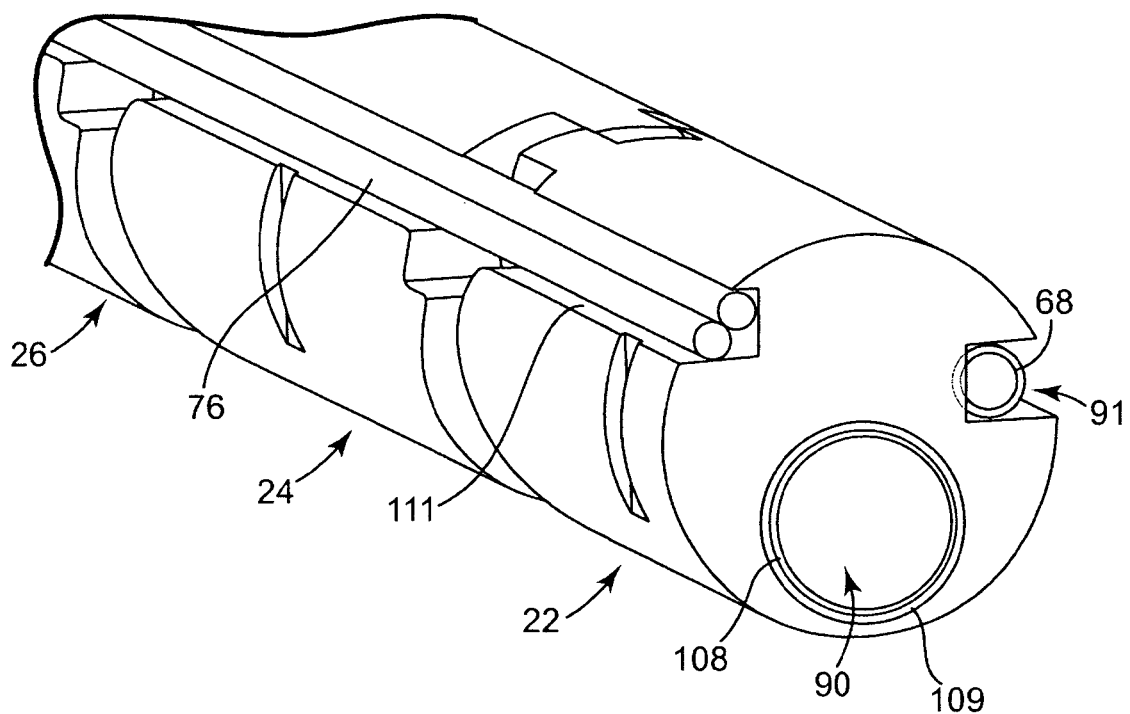
FIG. 13 is a plan view, from a distal end, of part of a distal portion of a surgical dissector and guide, in accordance with the present invention, showing a view from the distal end of a cross section through a middle segment (segment 22, in particular)

FIG. 13 illustrates a cross section of a middle segment, in particular segment 22. As illustrated in the embodiment shown in FIG. 13, one of the pistons 90 is disposed in a piston lumen 109 in segment 22, with the piston lumen 109 preferably running in the axial direction as shown and also radially offset as shown (with the dissector in the orientation shown in FIG. 1). The arrangement of the piston assembly 98 in the distal portion 16, with the pistons assembly 98 being axially offset as shown in FIG. 13, results in articulation of the segments of the distal portion 16. When the push/pull rod 92 is pulled proximally, the pistons 90 begin to articulate (curve upward as shown in FIG. 1) beginning with the most distal piston 90. So, preferably, the segments 20, 22, 24, 26 articulate beginning with the distal segment 20. As the distal portion 16 is straightened (when push/pull rod 92 is pushed distally), the segments 20, 22, 24, 26 straighten in the reverse order, beginning with the most proximal segment that is articulated.

Figure 39:
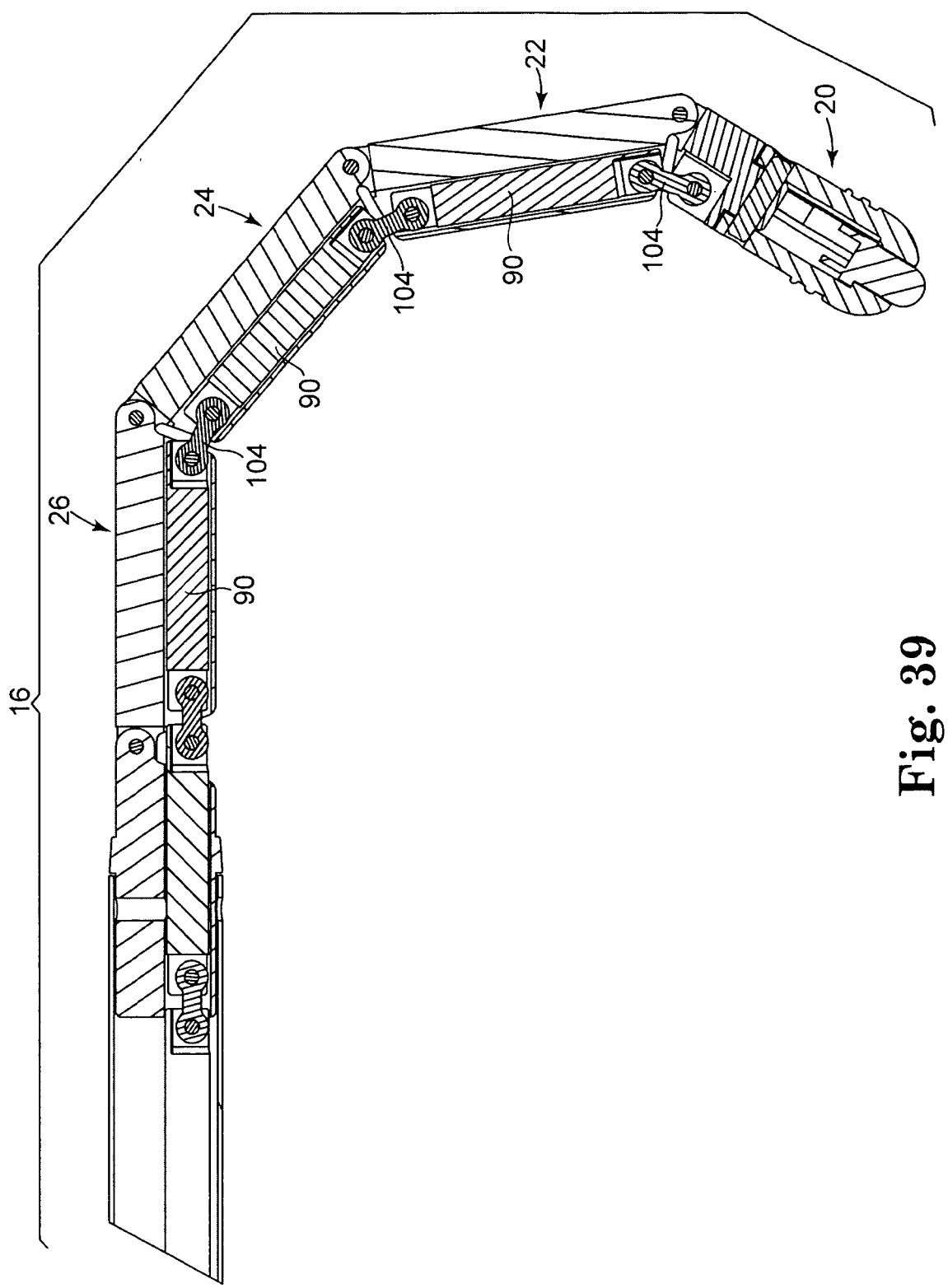
FIG. 39 is an illustration as in FIG. 38, showing a subsequent step in a progression of articulation from the distal segment proximally through multiple segments.

FIGS. 37-40 illustrate an exemplary, preferred progression of the articulation of the segment of the distal portion 16 of the shaft 12. FIG. 37 shows the distal segment 20 first articulated when the push/pull rod 92 is pulled proximally and a link 104 lines up with the joint 58 between the distal segment 20 and middle segment 22 and is able to articulate with the joint 58. Next, FIG. 38 shows that as the push/pull rod 92 is pulled proximally farther, the middle segment 22 also articulates when the link 104 on its proximal end lines up with the joint 58 between the middle segment 22 and segment 24. FIGS. 39 and 40 show subsequent steps as the push/pull rod 92 is pulled proximally until all segments 20, 22, 24, 26 are articulated with respect to the proximal portion 18 of the shaft 12.

The progression of articulation of the segments, as described above, is preferred for the embodiment described herein. However, other progressions are also contemplated by the present invention. For example, the segments could articulate from the proximal-most segment to the distal-most segment. This alternative progression of articulation can be possible if the lengths of the pistons 90 and links 104 are reconfigured to change the order in which the segments articulate. Also, other progressions are also possible with the segments articulating in any desired order by reconfiguring the lengths of the pistons 90 and links 104.

The embodiments of the invention illustrated in the figures show the segments articulating in the same general plane. However, it is also contemplated by the present invention that one or more of the segments may articulate out-of-plane. This could be possible by rotating the orientation of the joint 58 between adjacent segments. Such out-of-plane rotation of a segment(s) (e.g., the distal segment 20) could be advantageous for certain anatomy.

So as to reduce friction between the segments 22, 24, 26 and the pistons 90, a lubricious coating or a sheath is preferably coated, attached or deposited onto the pistons 90 and/or inside piston lumens 109. FIG. 12 shows three sheaths 108 that are preferably placed over each of the three pistons 90. The three sheaths 108 preferably comprise polytetrafluoroethylene (PTFE) heat shrink tubing cut to length, although other suitable materials may also be used. An alternative to the sheath 108, which is also contemplated by the present invention, is a lubricious coating coated or deposited onto the pistons 90 and/or inside of the piston lumens in the segments 22, 24, 26. Some examples of such lubricious coatings include, but are not limited to, Dicronite™, silicone, Teflon™, and other suitable polymers. The purpose of such coatings or sheaths is to reduce friction that occurs between similar materials rubbing on each other.

In order for the distal portion 16 of the dissector 10 to articulate as desired, the present invention is not limited to the assemblies discussed above. For example, instead of a piston assembly 98 disposed in the segments, a different assembly may be used. In the other contemplated assembly, stainless steel spring temper ribbon wire may be used. The ribbon wire may have varying thickness along the ribbon allowing for control of bending of the ribbon wire at certain locations along its length. For example, thinner sections of ribbon wire would be disposed in joint areas between segments of a distal portion 16. In addition, the ribbon wire may be over-molded with a lubricious material where the ribbon wire is disposed in the segments of the distal portion 16, so that the ribbon wire would be able to move through the segments. The described ribbon wire assembly could be pinned at both ends to the respective segments. Other configurations that allow for such movement of segments in the distal portion 16 are also contemplated by the present invention.

FIG. 13 also illustrates an example of how the guide wire tube 68 and the electrical wires 76 may extend through the segments 22, 24, 26. The guide wire tube 68 is shown extending through groove 91, which is also preferably radially offset, and the electrical wires 76 are shown extending through groove 111, which is also preferably radially offset (at a different location though).

The guide wire tube 68, electrical wires 76 and the push/pull rod 92 extend proximally through the tubular shaft housing 110 that comprises the proximal portion 18 of the shaft 12, and into the handle 14. In particular, the electrical wires 76 and push/pull rod 92 allow for the illumination source 32, and the articulating pistons 90 and segments in the distal portion 16 of the shaft 12 to be controlled proximally from the handle 14. The tubular shaft housing 110 provides a lumen 113 through which the other components may extend to the handle 14.

Referring back to FIG. 6, some components, that are located in the handle 14, are shown attached to the proximal end of the push/pull rod 92. The proximal end of the push/pull rod 92 is rigidly attached to a rack 112. The purpose of the rack 112 is to linearly move the push/pull rod 92 back and forth in the dissector 10, which in turn can articulate or straighten the piston assembly 98, and, ultimately, can articulate or straighten the segments 20, 22, 24, 26 of the distal portion 16 with respect to one another and the proximal portion 18 of the shaft 12. The rack 112 is preferably aligned such that the rack 112 moves back and forth along the length of the dissector 10. The rack 112, is preferably a generally oval-shaped component, as shown, with a set of teeth 114 on an inner surface 116 of the rack 112. In order to move the rack back and forth other components found in the handle 14 cooperate with the rack 112. The other components will be discussed below with regard to description involving figures illustrating the handle 14.

FIG. 6 also shows a link 118 and a jam bar 120. The link 118 is preferably a male threaded connector that screws into female voids (not shown), one such void in each of the rack 112 and the jam bar 120, and connects the rack 112 and jam bar 120 together. The purpose of the jam bar 120, and how it cooperates with other components, will also be discussed below.

Figure 14:
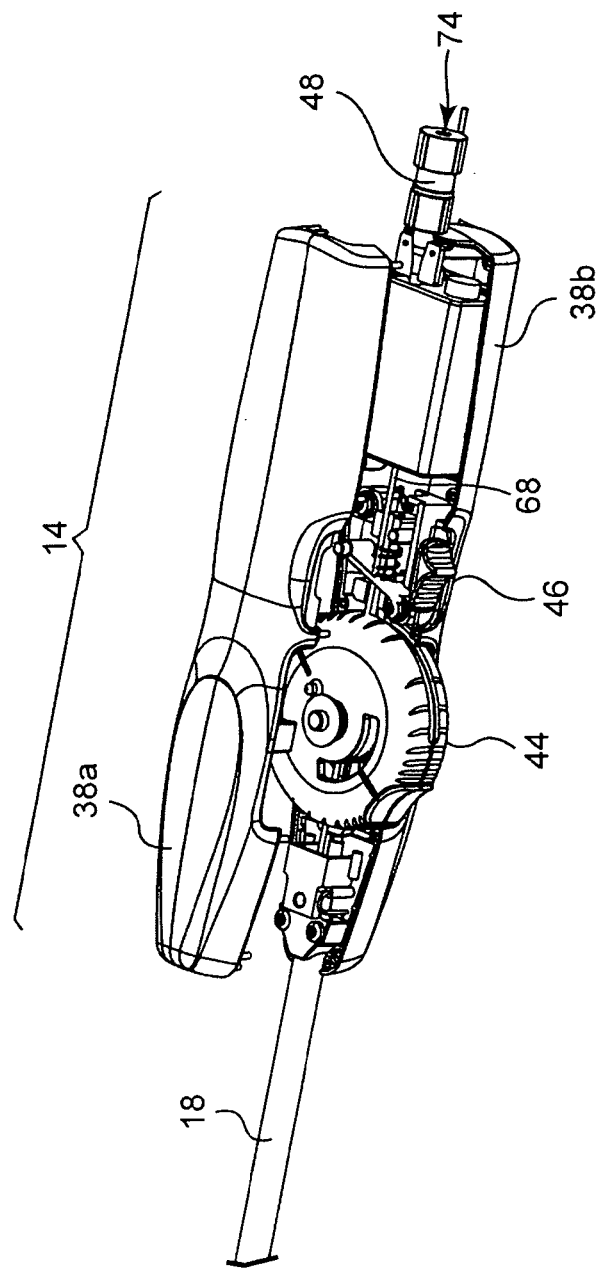
FIG. 14 is a plan view of a handle portion of the exemplary dissector and guide shown in FIG. 2, in accordance with the present invention, with a top half of a handle housing shown disassembled.

Details regarding the handle 14 and any exemplary enclosed or attached components will be discussed below. FIG. 14 illustrates generally an exemplary handle 14 (also shows part of the proximal portion 18 of shaft), in accordance with the present invention, shown with the top half 38*a* of the handle housing 38 removed.

Figure 15:
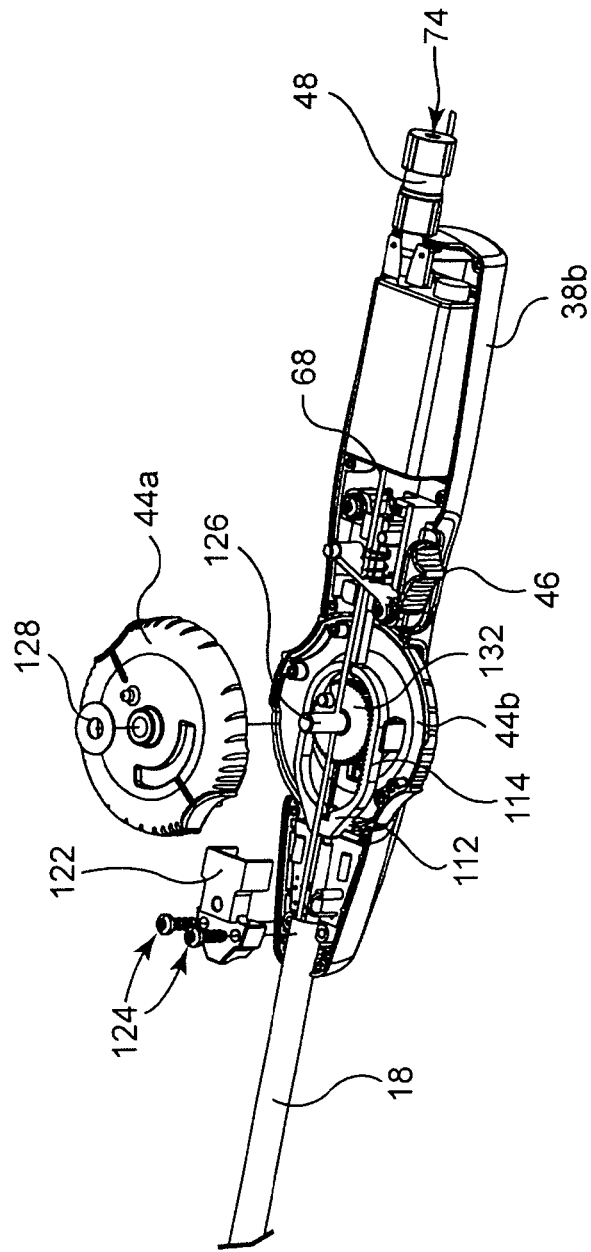
FIG. 15 is a plan view of the handle portion of the exemplary dissector and guide as shown in FIG. 14 with the top half of the handle housing removed and a top half of a control wheel and a shaft retainer both shown disassembled.

FIG. 15 is the same handle portion as shown in FIG. 14 with the top half 38*a* of the handle housing 38 removed and a top half 44*a* of the control wheel 44 and a shaft retainer 122 both shown disassembled. When assembled, the shaft retainer 122 is held in place in the handle 14 by two screws 124, and functions to rigidly attach the shaft 12 to the handle 14. The top half 44*a* of the control wheel 44 fits with the bottom half 44*b* over a dowel pin 126, and both halves 44*a*, 44*b* are held in place by the two halves 38*a*, 38*b* of the handle housing 38. The control wheel 44 rotates, which functions to move a pinion 126 with respect to the rack 112, which controls back and forth motion of the push/pull rod 92 and articulation and straightening of the distal portion 16 of the shaft 12 (more details of the components relating to the control wheel 44 will follow). In the particular embodiment shown in FIG. 15, washers (one shown as 128 and the other hidden in FIG. 15) provide space between the halves 44*a*, 44*b* of the control wheel 44 and the handle housing 38 such that the control wheel 44 may be allowed to rotate. However, other methods of allowing rotational movement of the control wheel 44 are also contemplated by the present invention.

Figure 16:
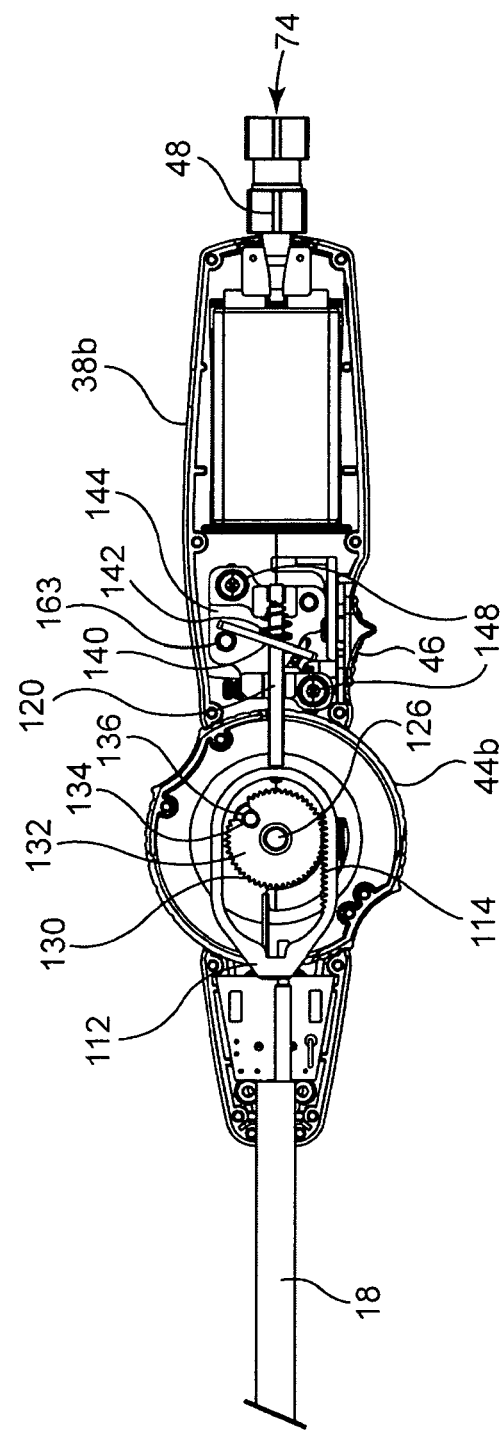
FIG. 16 is a top view of the handle portion of the exemplary dissector and guide as shown in FIG. 15 with the top half of the control wheel, the shaft retainer, and a portion of a guide wire tube removed.

FIG. 16 is a top view of the handle 14 portion as in FIG. 15. FIG. 16 shows how the teeth 114 on the rack 112 cooperate or fit together with a set of teeth 130 on a pinion 132. The pinion 132 includes a notch 134 into which a pin 136, also connected to both halves 44*a*, 44*b* of the control wheel 44, fits and holds the pinion 132. The pin 136 and notch 134 provide a way for the pinion 132 to move together with the control wheel 44 when rotated. Therefore, rotation of the control wheel 44 also rotates the pinion 132, which, through the cooperating sets of teeth 114, 130, moves the rack 112 backward and/or forward along the length of the dissector 10, which in turn pulls or pushes the push/pull rod 72 such that the attached pistons 90, and the corresponding segments 22, 24, 26, in which the pistons 90 are disposed, articulate or are straightened with respect to one another.

Figure 17:
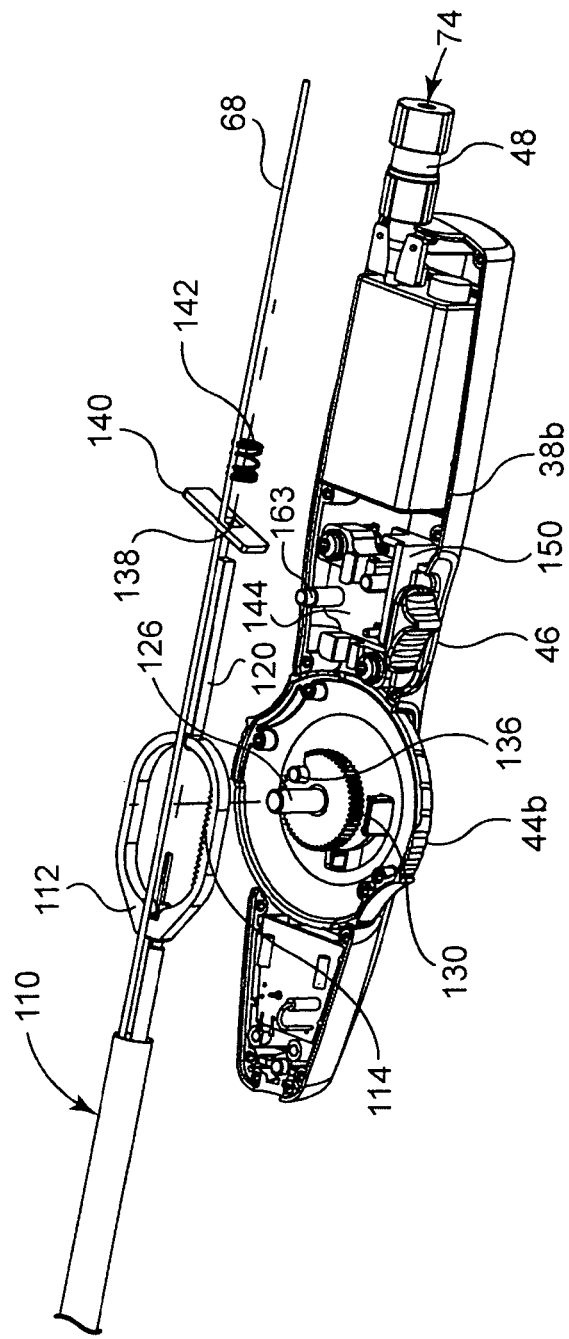
FIG. 17 is a plan view of the handle portion of the exemplary dissector or guide as shown in FIG. 15 with the top half of the control wheel and the shaft retainer removed and a shaft, the guide wire tube, a rack, a jam bar, a jam plate and a spring shown disassembled.
Figure 18:
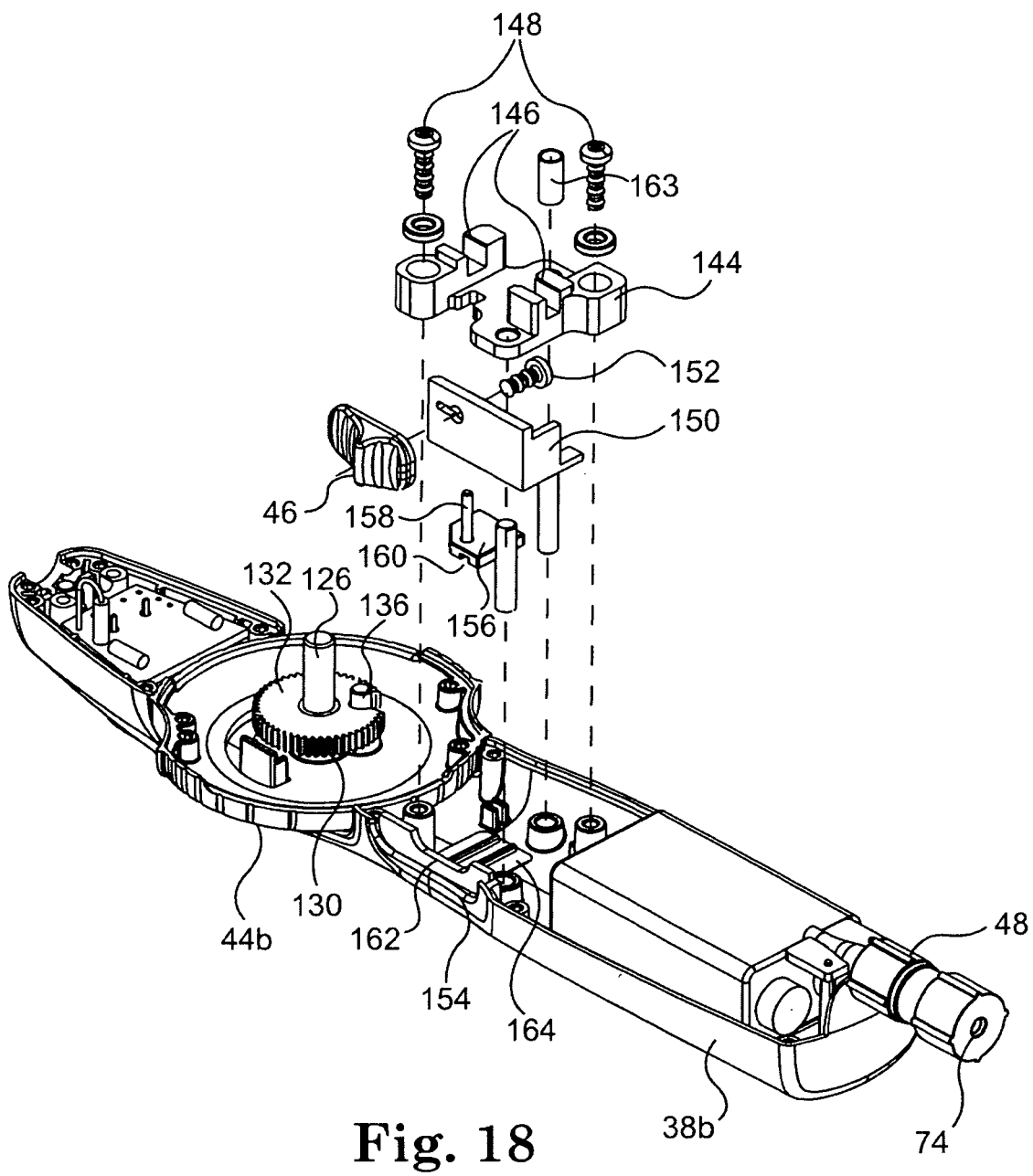
FIG. 18 is a plan view of the handle portion of the exemplary dissector or guide as shown in FIG. 17 with the shaft, the guide wire tube, the rack, the jam bar and the spring removed and a portion of a control wheel lock assembly shown disassembled.

In order to lock the distal portion 16 of the shaft 12 in a desired curve and/or in a substantially straight configuration, a locking mechanism is provided in the dissector 10 to selectively hold the push/pull rod 72 axially in an axial position. Locking the distal portion 16 in a desired configuration may be desired during certain procedures and in certain anatomical regions of a body. FIG. 16, together with FIGS. 17 and 18, illustrate an exemplary locking mechanism (i.e., an actuation mechanism lock) that may be used to hold the control wheel 44 in place and thereby hold the rack 112, push/pull rod 72, and thus the distal portion 16 of the shaft 12, in a desired configuration. In particular, the locking mechanism in the embodiment shown in FIGS. 16-18 comprises a friction lock. In general, it is desired that any locking mechanism used would preferably lock the distal portion 16 of the dissector 10 in a desired configuration and also unlock.

FIGS. 16-18 together show a friction lock and its components. The jam bar 120, which is attached to the rack 112, may extend through an aperture 138 in a jam plate 140.

The aperture 138 shown (FIG. 17) has a square shape, but other shapes are also contemplated (e.g., circular). The purpose of the aperture 138 is to allow the jam plate 140 to either contact the jam bar 120 or not, which locks or unlocks, respectively, the friction lock. The aperture 138 preferably has a diameter or other applicable dimension(s) that are slightly larger than the outer diameter or dimension of the jam bar 120 to allow the jam plate 140 (i.e., friction lock) to slide along the jam bar 120. A spring 142 surrounds the jam bar 120 on the proximal side of the jam plate 140. The purpose of the spring 142 is to maintain compression, as the dissector 10 may be used in various orientations. The jam bar 120, jam plate 140 and spring 142 are disposed in a housing 144. The jam bar 120 is shown extending through two channels 146 in the housing 144. The jam plate 140 and spring 142 are also disposed within the housing 144. The housing 144 is attached to the lower half of the handling housing 38*b* by two screws 148.

Figure 19:
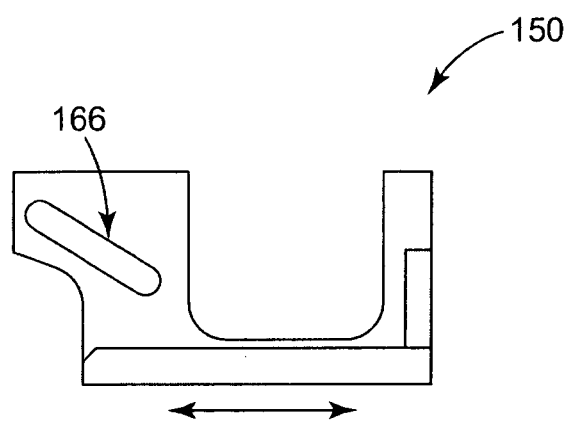
FIG. 19 is a top view of a cam plate (a component of the portion of the control wheel lock assembly shown in FIG. 18)

FIG. 18 provides an exploded view of a portion of the locking mechanism, as in FIG. 17, with the rack, 112, jam bar 120, jam plate 140 and spring 142 removed. The portion of the locking mechanism in FIG. 18 shows components that may function to move the jam plate 140 so the jam plate 140 either contacts the jam bar 120 or allows the jam bar to move through the aperture 138 in the jam plate 140, which locks or unlocks the friction lock, respectively. FIG. 18 illustrates that the lock switch 46 attaches to a cam plate 150 using a screw 152. The cam plate 150 and lock switch 46 together can move back and forth in an opening 154 in the handle housing 38*b*, which is oriented along the length of the dissector 10, in order to activate or inactivate the locking mechanism for the control wheel 44. In the exemplary locking mechanism shown in FIGS. 16-18, when the lock switch 46 is in a locked position, or moved toward the proximal end 50 of the handle 14, a follower plate 156 with an attached follower pin 158 are moved toward the jam bar 120 so the follower pin 158 allows the jam plate 140 to tilt against another pin 163 and frictionally engage the outer surface of the jam bar 120. The follower plate 156 includes grooves 160 that mate with grooves 162 (as shown) on a rail plate 164 that is attached to the bottom half 38*b* of the handle housing 38. As seen in FIG. 19, which shows the cam plate 150, there is a slot 166 in the cam plate 150 in which the follower pin 158 rides (the slot being angled at about a 45 degree angle from the direction that the cam plate 150 moves along the length of the dissector 10, with the general direction being indicated by the double-ended arrow in the figure). As the cam plate 150 is slid along the length of the device, the described configuration results in the follower plate 156 and pin 158 moving generally perpendicular to the direction of the lock switch 46 and cam plate 150 (which is along the length of dissector 10). The result is that the follower pin 156 may be pushed against the jam plate 140 in such a way to move the jam plate 140 to either allow the jam bar 120 to pass through the aperture 138 or not. When the lock switch 46 is in an unlocked position, or moved toward the distal end 36 of the handle 14, the follower pin 158 is moved away from the jam bar 120 through the slot 166 in the cam plate 150, which moves the jam plate 140 such that the jam bar 120 is able to move freely though the aperture 138 in the jam plate 140. A purpose of the configuration chosen for the locking mechanism is to translate movement of the switch 46 that goes along the length of the dissector 10 to movement that is perpendicular to the movement of the switch 46.

In the exemplary embodiment of the locking mechanism described above, once the dissector 10 is properly positioned, the locking mechanism may be activated. In this preferred embodiment, the control wheel 44 may still be rotated to further articulate the segments of the distal portion 16, but the control wheel 44 cannot be rotated in a direction to straighten the segments. Other embodiments are, however, contemplated that would also include preventing further articulation of the segments when a locking mechanism is activated.

The exemplary locking mechanism described above is just one example of a locking mechanism that may be used in the present invention, and many other locking mechanisms are also contemplated by the present invention (e.g., a ratchet system or a cam mechanism).

Figure 20:
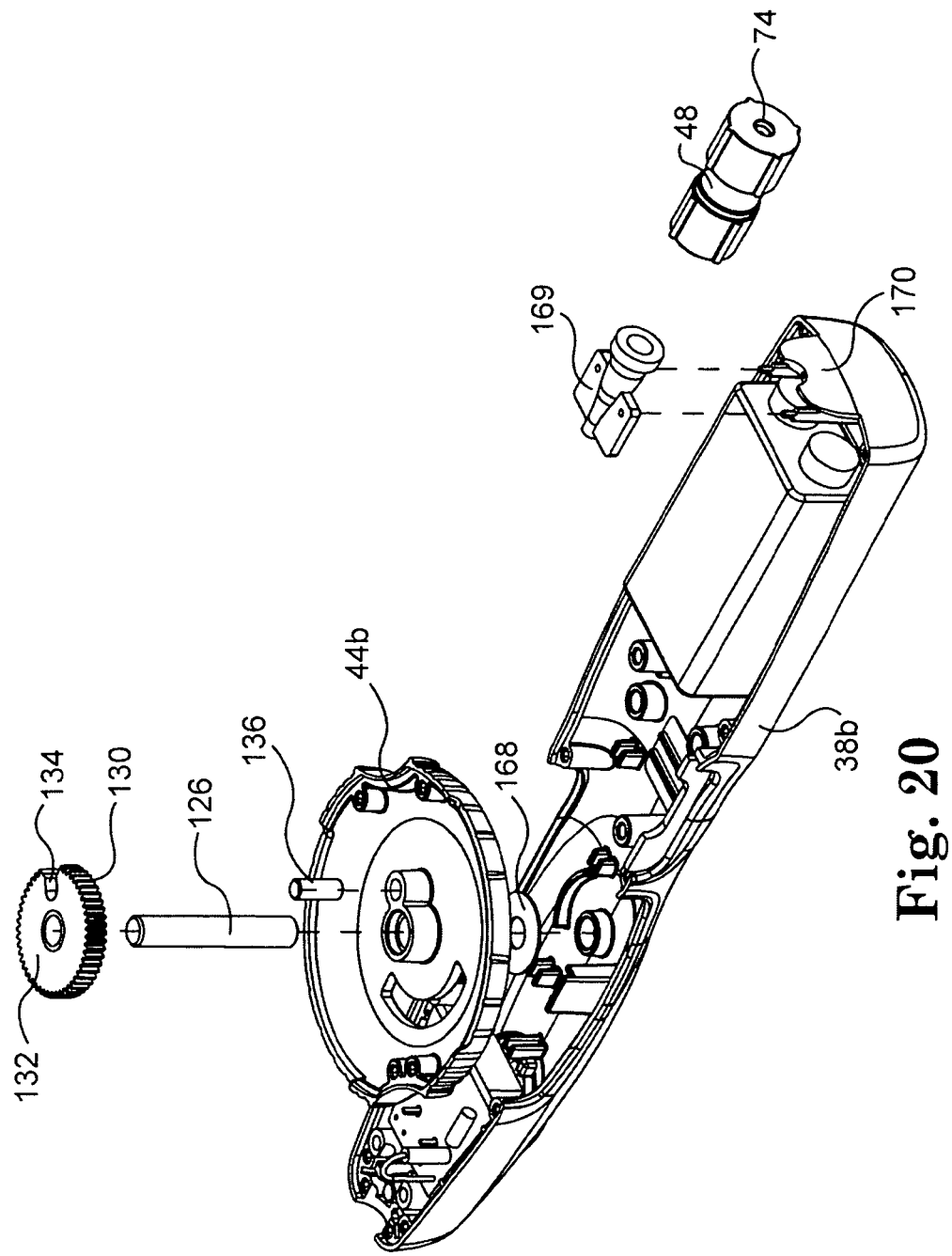
FIG. 20 is a plan view of the handle portion of the exemplary dissector and guide as shown in FIG. 18 with the portion of the control wheel lock assembly removed and a pinion, pins, a bottom half of the control wheel, and a guide wire lock shown disassembled.

FIG. 20 is the same embodiment of the handle 12 as in FIG. 19, except the locking mechanism components of FIG. 19 are removed, and the pinion 132, dowel 126, lower half of the control wheel 44b, a washer 168, a female luer 169, and the guide wire lock 48 are shown disassembled. The figure illustrates a second washer 168 that is placed on the dowel pin 126 between the lower half 38b of the handle housing 38 and the lower half 44b of the control wheel 44 such that, along with the other washer 128 (in FIG. 15), the control wheel 44 may be free to rotate inside the handle housing 38 on the pin 126. The purpose of the second washer 168, just like the first washer 128, is to allow the control wheel 44 to rotate freely with respect to the handle housing 38 (38b in particular with respect to the second washer 168). FIG. 20 also illustrates that the guide wire lock 48 is retained in the handle 14 by being attached to the female luer 169 that is held between a guide wire lock retainer 170 and the top half 38a (not shown) of the handle housing 38.

Figure 21:
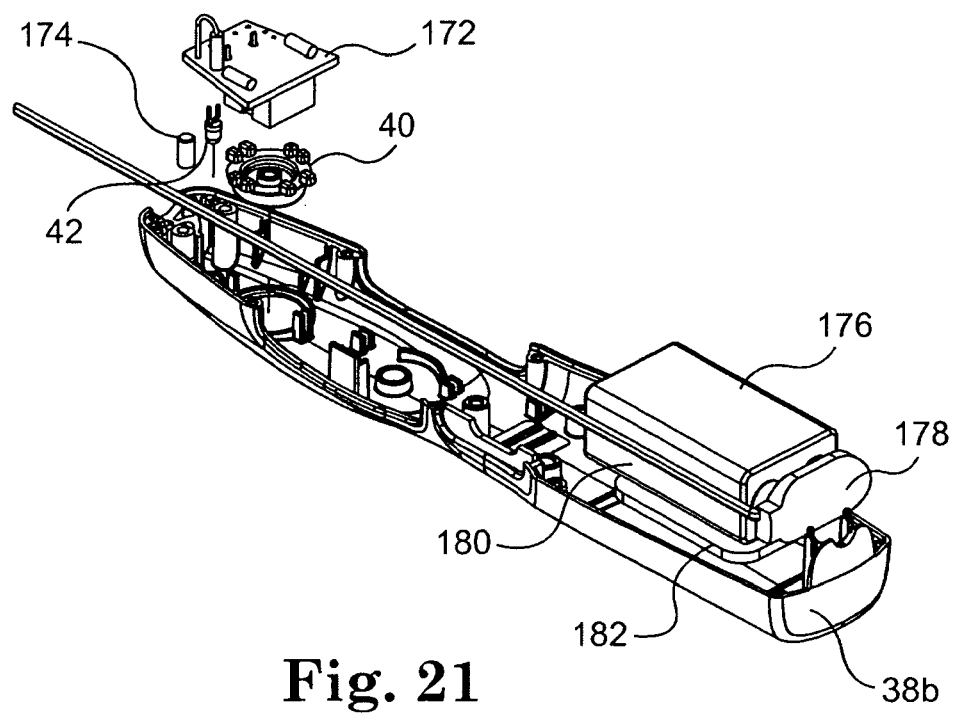
FIG. 21 is a plan view of the handle portion of the exemplary dissector and guide as shown in FIG. 20 with the pinion, the pins, the bottom half of the control wheel and the guide wire lock removed and a power source, power source wires, a power source connector, a PCB, an illumination source on-off switch, an illumination source indicator light, a shaft retainer pin, and a power source stabilizer shown disassembled.

FIG. 21 is an exemplary portion of the device shown in FIG. 20 with the components shown disassembled in FIG. 20 removed in this figure, and with a printed circuit board (PCB) 172, the illumination source on/off switch 40, the illumination source indicator light 42, a shaft retainer pin 174, a power source 176, a power source connector 178, power source wires 180, and a power source stabilizer 182 shown disassembled from the bottom half 38b of the handle housing 38. The purpose of the power source 176 is to provide power for the PCB 172, and ultimately the illumination source 32 and illumination source indicator light 42. The power source 176 in the portion of the exemplary dissector 10 shown in FIG. 21 is a 9-volt battery. Other power sources, however, are also contemplated by the present invention. Preferably, the power source 176 is a disposable battery. The disposable battery may be a disposable lithium battery. The power source 176 may be capable of powering the illumination source 32 and the illumination source indicator light 42 to a desired intensity for any determined time period. The power source may be removable. The connector 178 and the power source wires 180, in the preferred embodiment shown in the figure, extend and attach to the PCB circuit 172. Electrical wires (not shown in the figure) extend from the PCB circuit 172 to the illumination source indicator light 42 and (wires 76) to the illumination source 32 in the distal tip 30 of the shaft 12. In order to stabilize the power source 176 in the handle housing 38 and prevent movement of the power source 176 in the handle 14, the power source 176 may be attached to the power source stabilizer 182, as in FIG. 21. The power source stabilizer 182 may comprise, for example, a foam spacer (as shown in figures), hot glue, a spring, or any other suitable material or form for a given application. FIG. 21 also includes the shaft retainer pin 174 that prevents the tubular shaped shaft 12 from rotating.

Figure 22:
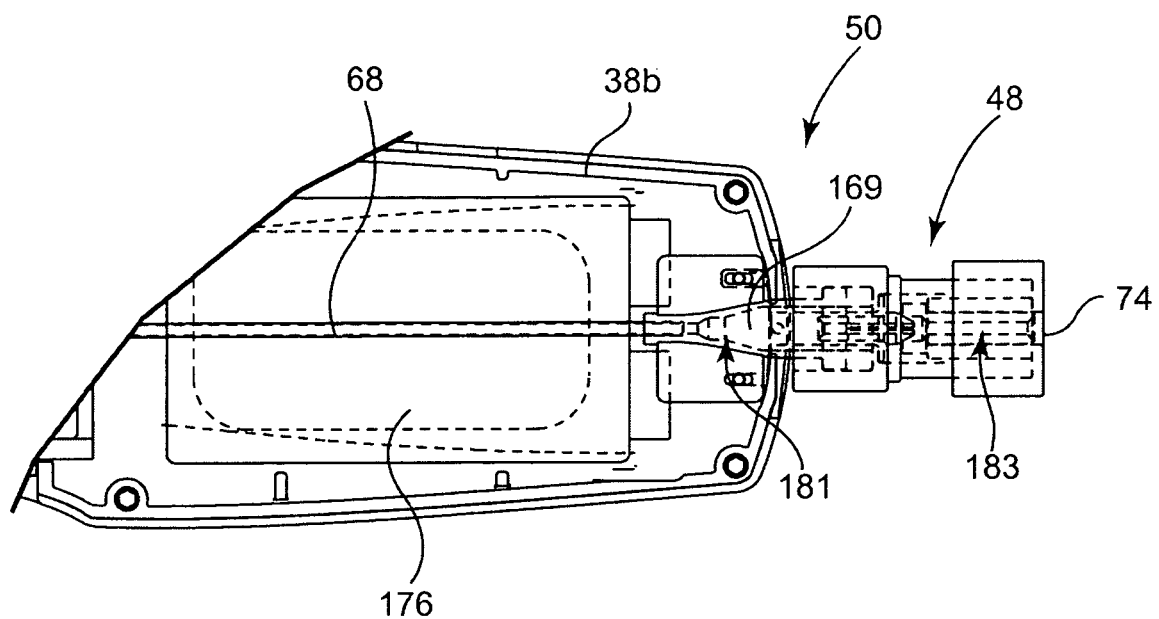
FIG. 22 is a top view of a proximal portion of a handle of an exemplary dissector and guide, in accordance with the present invention, shown with a top half of a handle housing removed.

FIG. 22 is a top view of a portion of the handle 14 near the proximal end 50 shown with the top half 38a of the handle housing 38 removed. The figure illustrates that the guide wire tube 68, in the exemplary embodiment, extends through the handle 14 such that it extends by the power source 176 toward the top half 38a of the handle housing 38. The figure also illustrates how the guide wire tube 68 extends into the female luer 169. A guide wire may continue out the opening 74 through a lumen 181 in the female luer 169 and through a lumen 183 in the guide wire lock 48 to the proximal opening 74.

Another feature of the present invention is that the dissector 10 may include an indicator, preferably on the handle 14, to indicate to the user to what extent the distal portion 16 is curved or articulated. The purpose of such an indicator is to inform the user of the amount of curvature of the distal portion 16, which may be important for a given procedure or with regard to a particular anatomical position. For example, the control wheel 44 may have tactile features that indicate to the user to what extent the distal portion 16 of the shaft 12 is deflected or articulated. Additionally, or alternatively, the handle 12 may include a graphical angle indicator or indicators that coordinate with the rotation of the control wheel 44 to indicate the amount of articulation of the distal portion 16, such as that shown as 230 in FIG. 1. In the embodiment shown in FIG. 1, as the control wheel 44 is rotated, an indentation on the control wheel 44 may generally line up with one of three graphical indicators 230, which graphically illustrate the approximate amount of articulation of the distal portion 16 of the shaft 12. Other types of indicators are also contemplated by the present invention.

Figure 23:
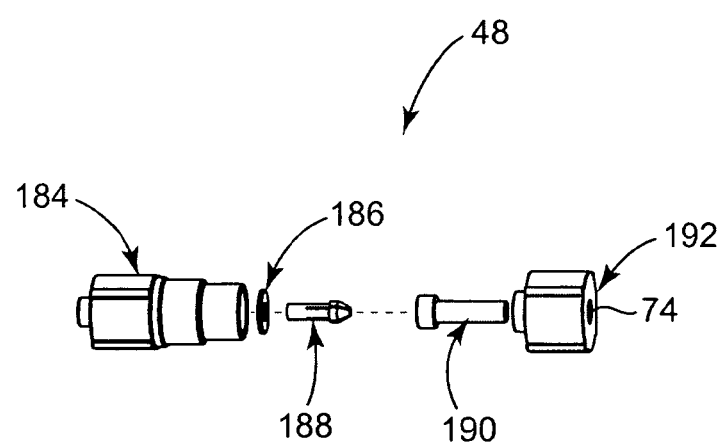
FIG. 23 is an exploded view of an exemplary guide wire lock, in accordance with the present invention.

FIG. 23 is an exploded view of the exemplary guide wire lock 48. A purpose of the guide wire lock 48 may be to hold or lock (and also release or unlock) a guide wire positioned through the guide wire tube 68 of dissector 10 in a desired position or location. A purpose for locking the guide wire in place is discussed below with regard to a method embodiment of the present invention. The exemplary guide wire lock 48, although other embodiments are also contemplated, comprises a fitting 184, a washer 186, a collet 188, an insert 190, and a knob 192. A lumen 183 extends through each of the components of the guide wire lock 48, providing a space for a guide wire to move through the guide wire lock 48. However, a portion of the lumen 183 may also be closed if the guide wire lock 48 is in a locked configuration. A guide wire may be locked into a position, for example, by turning the knob 192 clockwise, which tightens the lock 48 around the guide wire. In particular, the fitting 184 and knob 192 are cooperatively threaded (not shown) such that when the knob 192 is turned clockwise, it moves closer to the fitting 184, which in turn moves the collet 188 into the insert 190. The collet 188 has any number of slots such that when the collet 188 is moved into the insert 190 the collet 188 is radially compressed. The collet 188 is also preferably made of a lubricious polymer (e.g., Delrin™, PEEK™, or certain grades of nylon), such that the collet 188 is able to move as necessary within the other components of the guide wire lock 48. Therefore, if a guide wire extends through the lumen 183 that runs through the collet 188, the guide wire may be held in place by the compressed collet 188.

The dissector 10, as described above, may be used to dissect tissue. Additionally, or alternatively, the dissector 10 may be part of a system, including other components or devices, used to guide another medical device into a desired location in a body. Other components or devices that may be used with the dissector 10 comprise a guide wire (example is 218 in FIGS. 32-35), a guide member 194, and another medical device (e.g., an ablation device 222 as in FIG. 35) that is to be placed in a location in a body.

In general, the guide wire, as part of the system, may be used to guide a medical device to a desired location in a body. More detail of how the guide wire is used in the system in accordance with the present invention is provided below. However, in general, a distal end of the guide wire is fed through the guide wire tube 68 in the dissector 10 from opening 74 and out through opening 72, after the distal portion 16 of the dissector 10 is in a desired location in a body. The distal end of the guide wire may then be attached to the guide member 194 (having first and second ends) at a first end and then withdrawn back through the guide wire tube 68 until the guide member 194 comes near or into contact with the distal tip 30 of the dissector 10. The guide wire is then locked using the guide wire lock 48, and the dissector 10 and guide wire, with guide member 194 attached are withdrawn back through an port of entry. The dissector 10, guide wire and attached guide member 194 may pull another medical device, which may be attached to the second end of the guide member 194, into the location in the body where the distal portion 16 of the dissector 10 was located prior to withdrawal.

In the present invention, any type of known or future developed guide wire may be used with the system. An exemplary guide wire is a floppy, straight-tip, 0.035" guide wire. The guide wire may include markings to gauge the amount of guide wire being extended through and out from the dissector 10, which can assist in medical device placement procedures, for example.

Figure 24:
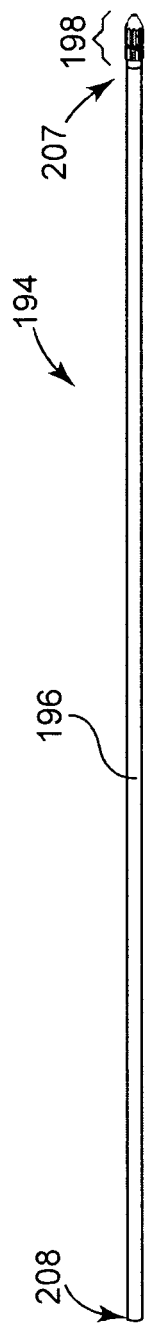
FIG. 24 is a plan view of an exemplary guide member, in accordance with the present invention.

FIG. 24 illustrates an exemplary guide member 194. The purpose of the guide member 194 is to guide a medical device to a desired location. As part of the system, in accordance with the present invention, the guide member attaches, at one of two ends, to a guide wire that is withdrawn back through the dissector 10 through which the guide wire is fed. The second end of the guide member 194 is preferably attached to a medical device that is desired to be placed in a body. Therefore, when the guide wire is withdrawn, the guide member is pulled into the body adjacent the distal tip 30 of the dissector 10. The guide wire is locked in place in the dissector 10 and then the dissector and wire are withdrawn, which pulls the guide member through, and ultimately pulls a medical device that may be attached to the second end of the guide member into a desired location in a body.

Figure 25:
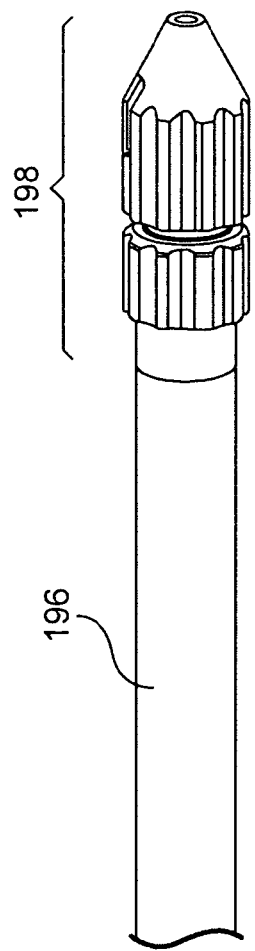
FIG. 25 is a plan view of a torquer end of the exemplary guide member shown in FIG. 24.
Figure 26:
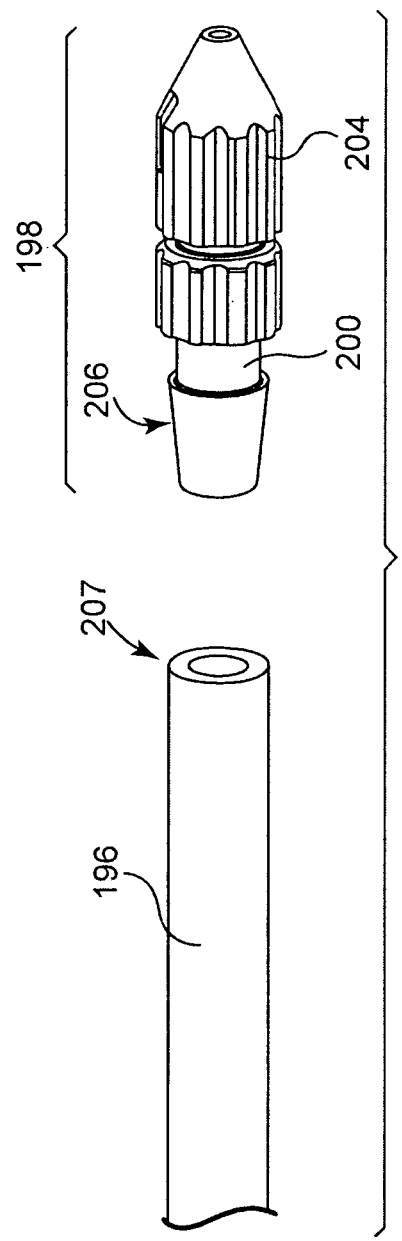
FIG. 26 is a plan view of the torquer end of the exemplary guide member shown in FIG. 24, shown with a tube portion of the guide member removed from the torquer.
Figure 27:
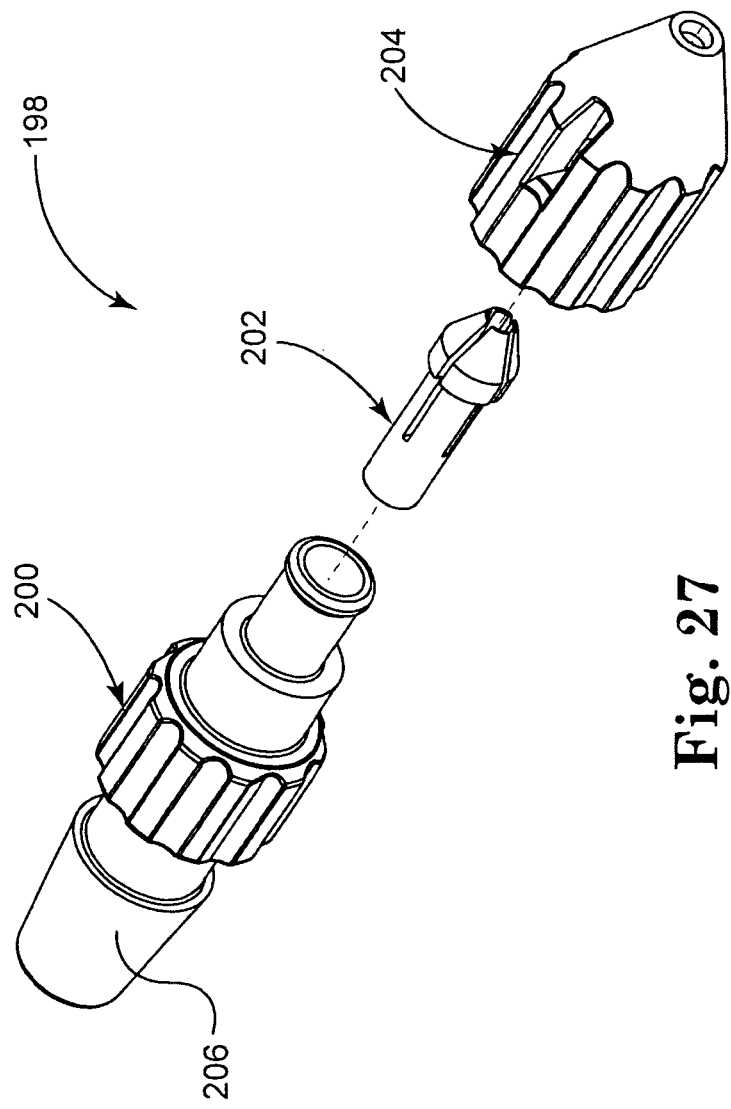
FIG. 27 is an exploded view of the torquer end of FIG. 26.

The exemplary guide member 194 comprises an elongate tube 196 with a torquer 198 on a first end 207 of the tube 196 (having first 207 and second 208 ends). FIG. 25 illustrates the end of the guide member 194 including the torquer 198. The torquer 198 has configurations such that it may retain guide wire and may, with a change in configuration, release the guide wire. FIG. 26 includes the same portion of the guide member 194 as in FIG. 24 with the torquer 198 removed from the tube 196. FIG. 27 is an exploded view of the torquer 198, which comprises a torquer body 220, collet 202, and torquer tip 204. The tapered end 206 of the torquer body 200 preferably fits inside the tube 196 in order to hold the torquer 198 in place in the tube 196. The guide wire member 194, preferably, may be used to lock and release an end of a guide wire in the torquer 198 or may otherwise be capable of attaching or coupling to the distal portion 16 of the dissector 10. Moreover, the guide wire member 194, preferably, may, on the other end of the tube 208 (as seen in FIG. 24), reversibly hold a medical device that is desired to be guided into or placed in a location in a body.

The torquer 198 may retain a guide wire, or lock the guide wire in place, by radially compressing the guide wire within a lumen running through the torquer 198. the torquer tip 204 is cooperatively threaded to the torquer body 200 (not shown), such that when the torquer tip 204 is turned (e.g., clockwise) the torquer tip 204 moves closer to the torquer body 200, which in turn causes the collet 202 (which is attached to the torquer body 200) to be pushed into the tip 204 and compressed in the tip 204 in an accordingly shaped orifice (not shown) in the tip 204. The collet 202 has any number of slots that allow the collet 200 to be radially compressed. The collet 202 is also preferably made of a lubricious polymer (e.g., Delrin™, PEEK™, or certain grades of nylon), such that the collet 202 is able to move as necessary within the other components of the torquer 198. Therefore, a guide wire running through a lumen in the torquer 198, and collet 202, may be compressed and held in place.

Preferably, the torquer 198 and the end 208 of the guide member 194 may both be sized and shaped to pass through a small thoracotomy incision (e.g., roughly 1 cm, and/or a 10 or 12 mm trocar port). The guide member 194 may have a length sufficient to enter a superior thoracic incision, pass around one or more anatomic structures of the heart and then exit an inferior thoracic incision, whereby both ends of the guide may be visible ex vivo or outside the patient's body (e.g., roughly 16" to 18"). The guide member 194 may have a smooth shape to allow its passage around various anatomic structures while not causing substantial tissue damage. The guide member 194 may have one or more portions that have a durometer range of about 40 to 90 shore A.

Figure 28:
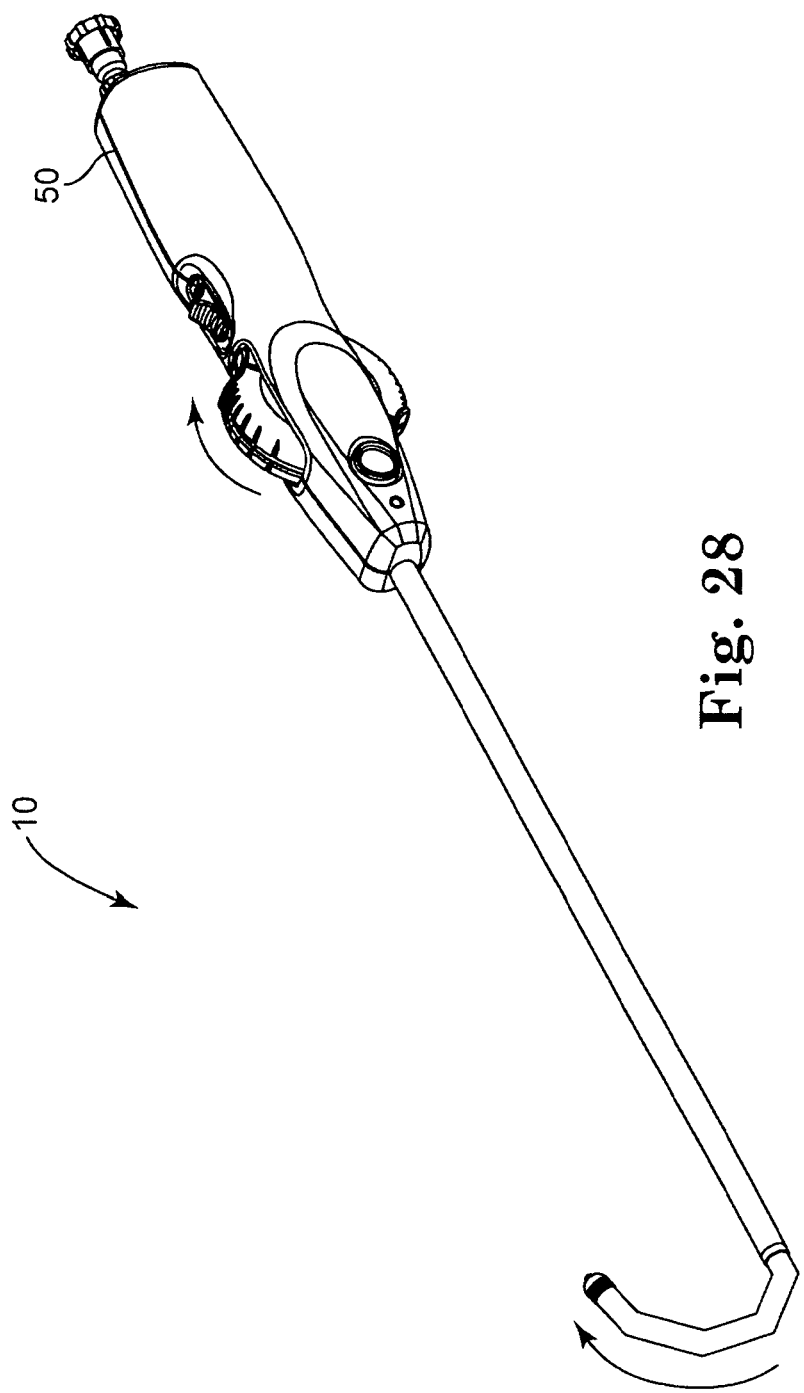
FIG. 28 is a plan view of an exemplary dissector and guide, in accordance with the present invention, with arrows showing rotation of a control wheel toward a proximal end of a handle and resultant articulation or curving of a distal portion.
Figure 29:
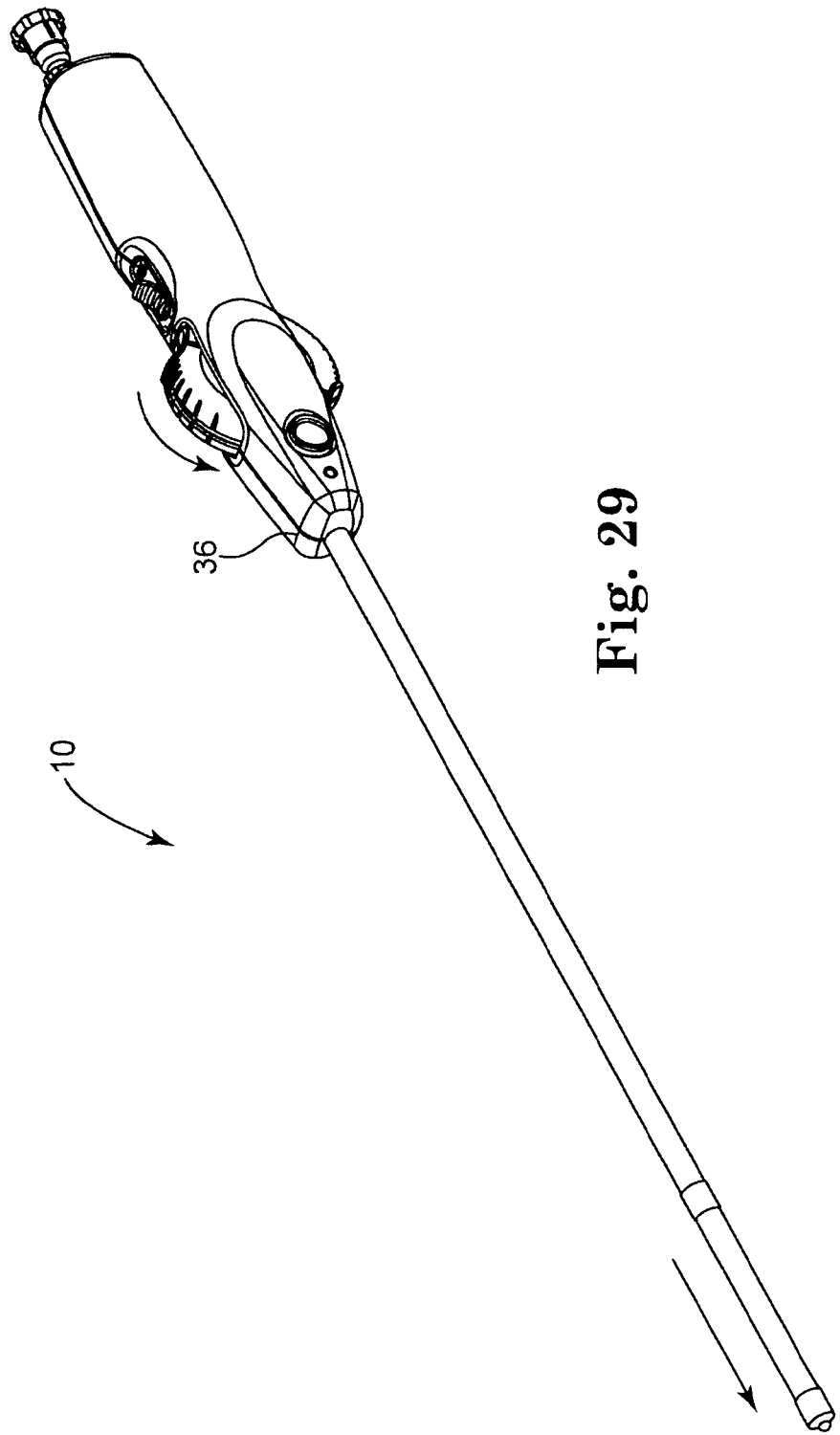
FIG. 29 is a plan view of the exemplary dissector and guide of FIG. 28, with arrows showing rotation of the control wheel toward a distal end of the handle with resultant straightening of the distal portion.

FIG. 28 illustrates (with arrows) how, in an exemplary embodiment of the present invention, rotating the control wheel 44 towards the proximal end 50 of the handle 14 curves or articulates the distal portion 16 of the shaft 12 of the dissector 10 into a curved configuration. As shown in FIG. 29, rotating control wheel 44 towards the distal end 36 of the handle 14 returns the dissector 100 to its original configuration, i.e., straightens out the distal portion 16. Although not shown in FIGS. 28, 29, graphical indicators on the handle 14 may be included that correlate to the amount of curvature of the distal portion 16 based on the amount of control wheel 44 rotation.

For use in cardiac procedures, such as those treating arrhythmias of the heart as described above, the overall length of the dissector 10 may preferably be roughly less than or equal to 70 cm. The useable shaft 12 length including an articulating distal portion 16 at 0 degrees may be roughly less than or equal to 50 cm. The shaft 12 is preferably of suitable length to allow a surgeon to position the distal portion 16 of the dissector 10 behind and around anatomic structures of a beating heart without unintended tissue damage. The handle 14 length may be roughly less than or equal to 30 cm. The handle 14 outer diameter, where the handle 14 is to be gripped by the operator, may be roughly be 2.5 to 5 cm. The shaft 12 outer diameter may be roughly 0.250" to 0.4375". The length of the distal portion 16 having the ability to be articulated may be about 5 cm to 15 cm. The range of motion of the articulating distal portion 16 may have a range of motion of about 0 to at least 180 degrees and, in one embodiment, not more than 180 degrees and, in another embodiment, between 0 and 165 degrees. The variable radius of articulation of the distal portion 16 may have a minimum radius of about 2.5 cm, when articulated at about 165 degrees, thereby allowing proper positioning around certain anatomic structures, e.g., cardiac structures.

The present invention also includes a method of using the dissector 10 and the other components of the system, and a method of dissecting and/or guiding a medical device (e.g., ablation device) into a body. One exemplary method using minimally invasive techniques is described below with reference to FIGS. 30-36. However, other methods, using different points of entry or an open surgical approach, for example, are also contemplated by the present invention.

Figure 30:
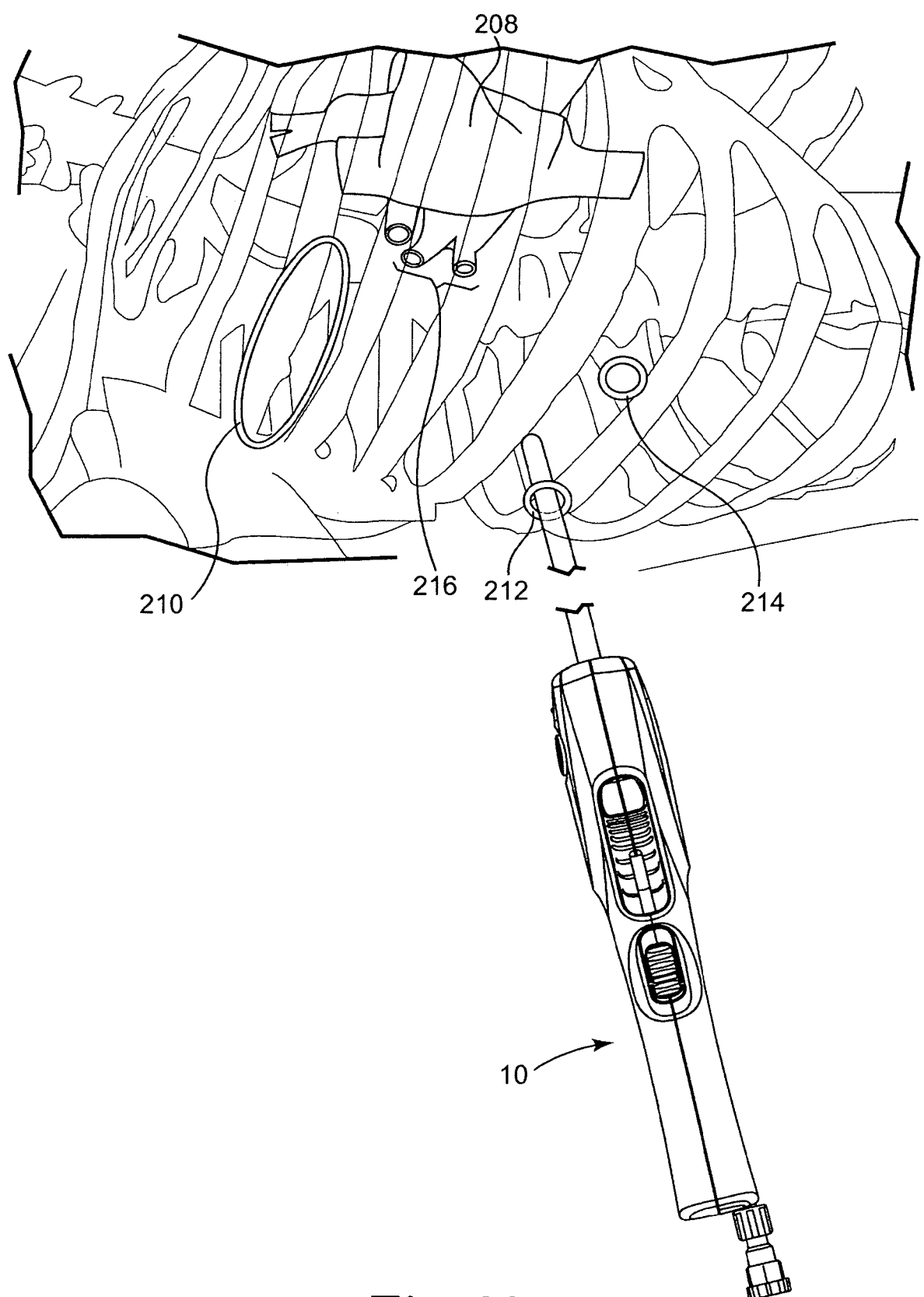
FIG. 30 is an illustration of a chest cavity of a patient from the right side shown with a thoracotomy and two ports to access the heart shown inside, and showing a distal portion of a shaft of an exemplary dissector and guide, in accordance with the present invention, entering one of the ports.

FIG. 30 is an illustration of a chest cavity of a representative patient with a view from the right side of the patient. FIG. 30 includes a view of the heart 208, a thoracotomy 210 and first and second ports 212, 214, respectively. FIG. 30 also illustrates a first step in a procedure or method of using the dissector 10 of the present invention for an ablation procedure, and pulmonary antrum isolation, in particular. As can be seen in FIG. 30, the distal tip 30 of the shaft 12 is first inserted through a first port 212, or pericardial incision, that provides access to the heart. The first port 212 may be a roughly 1 cm incision or a 10 mm trocar port, for examples, although other sizes are also contemplated. The distal portion 16 of the dissector 10 is in a substantially straight configuration so that the distal portion 16 may pass easily through the port 212. The dissector 10 is then advanced into the body so that the distal tip 30 is near the area of the pair of pulmonary veins 216 on the right side of the heart and near the pericardial reflections (on the back side of the heart, and not seen in Fig.) that generally need to be dissected to place an ablation device properly in pulmonary antrum isolation procedures. The illumination source 32 of the dissector 10 may be illuminated to help confirm the location of the distal tip 30. The distal tip 30 may be used to create a passageway through the pericardial reflections by perforating the pericardial reflections with the tip 30.

Figure 31:
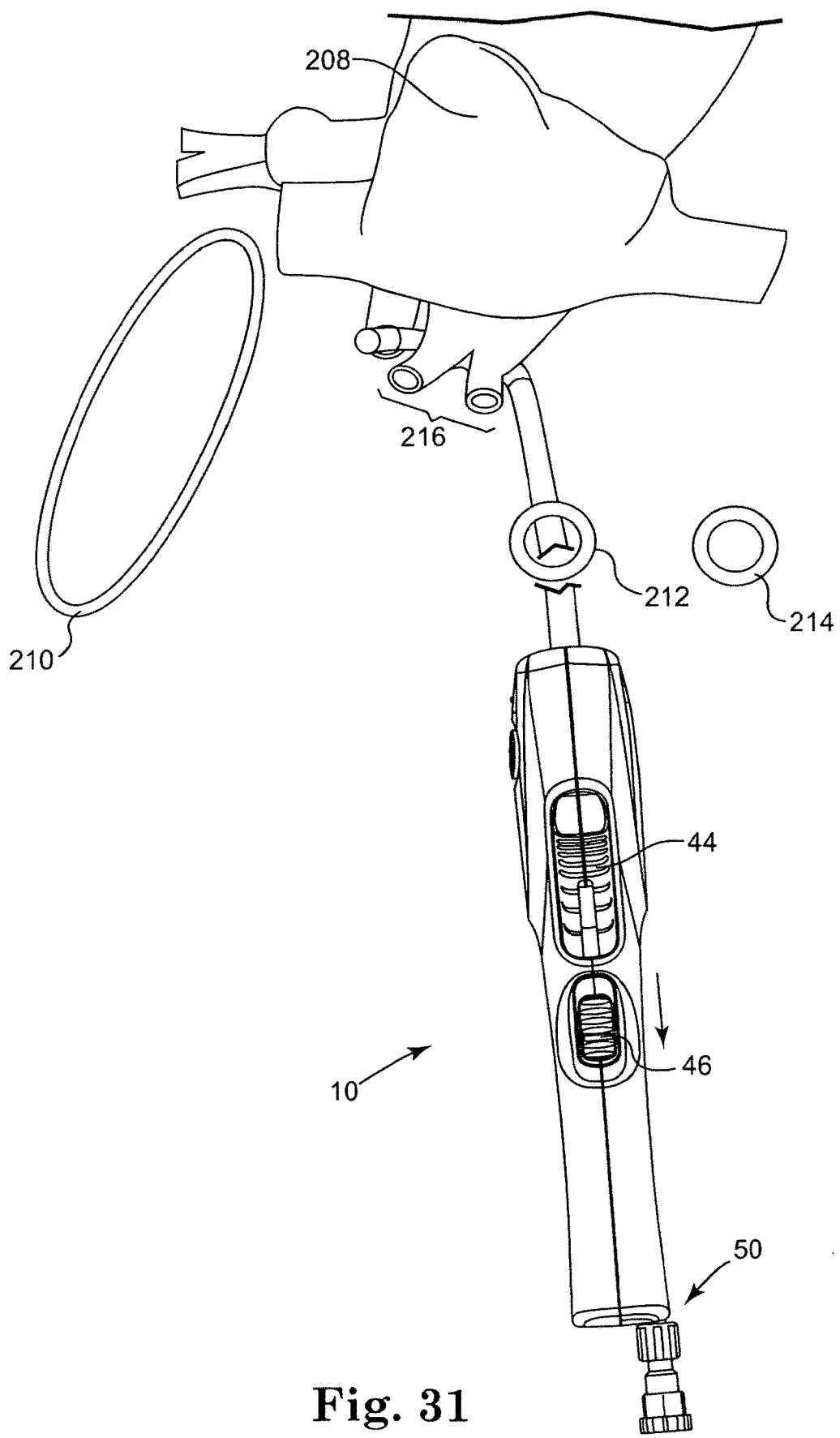
FIG. 31 is an illustration as in FIG. 30, with a close-up view of the ports, heart, throracotomy etc. and showing the distal portion of the shaft of the exemplary dissector and guide inserted and articulated around a pair of pulmonary veins on the right side of the heart, and, as indicated by the arrow, an articulation locking mechanism switch moved to prevent the distal portion from straightening.

FIG. 31 illustrates a next step in the method of using the dissector 10 for pulmonary antrum isolation. Once the distal tip 30 is in the desired location near the pulmonary veins 216, as shown, the control wheel 44 is rotated toward the proximal end 50 of the handle 12, which articulates the distal portion 16 of the shaft 12 of the dissector 10 around the pulmonary veins 216. The articulation lock 46 is then moved to a locked position (as indicated by the arrow) so that the distal portion 16 may stay in the desired articulated position around the pulmonary veins 216 and will not straighten until desired.

Figure 32:
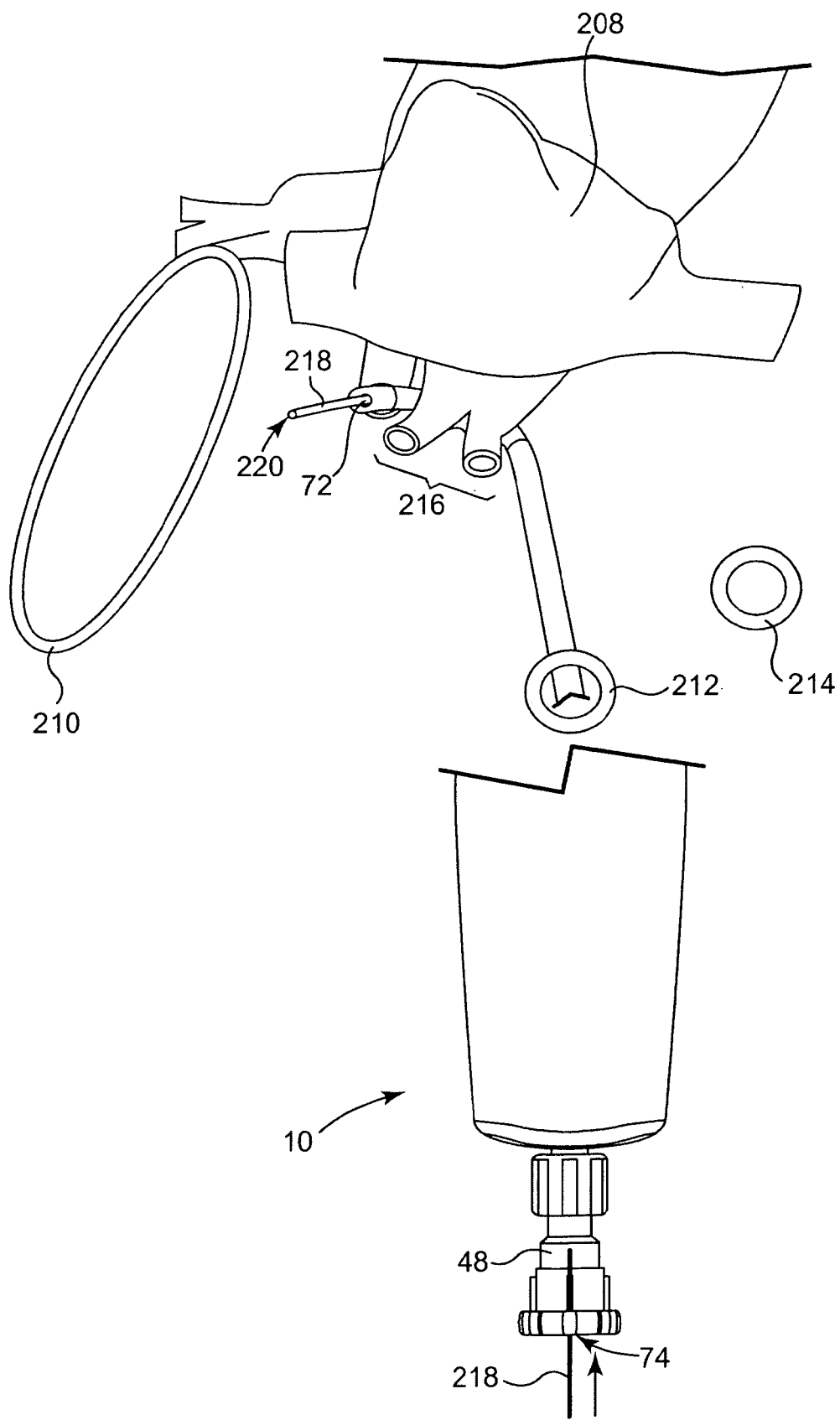
FIG. 32 is an illustration as in FIG. 31, and showing a guide wire being fed through a guide wire tube in the exemplary dissector and guide and exiting the distal end of the dissector and guide.

FIG. 32 illustrates the next step in the method, which is to place a guide wire 218 in the opening 74 (shown by arrow) and extend the guide wire 218 through the guide wire tube 68 so that the distal end 220 of the guide wire 218 extends out (e.g., by approximately 1 cm) the distal end of the guide wire tube 68, or opening 72, in the distal tip 30, as shown. The guide wire 218 is then extended out through the thoracotomy 210 where it is to be connected to a guide member 194 (not shown in Fig.). Although the exemplary method involves extending the guide wire 218 out through the thoracotomy 210, the guide wire 218 could alternatively extend out of the body through a smaller opening or port. If so, it may be necessary to use a surgical forceps to reach into the opening or port and grab the distal end 220 of the guide wire 218 and pull it out through the port, where it could be attached to a guide member 194.

Figure 33:
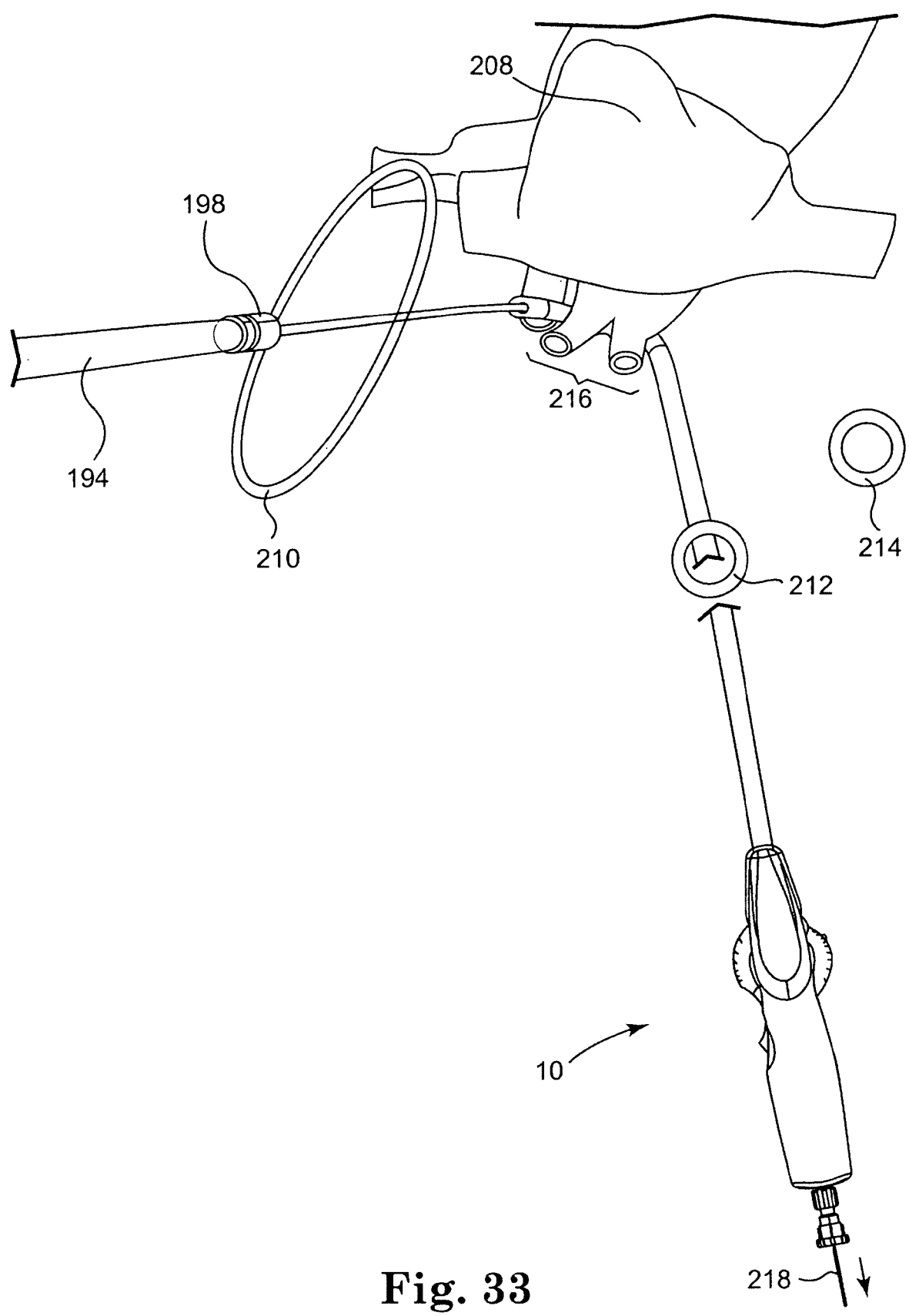
FIG. 33 is an illustration as in FIG. 32, and showing the end of the guide wire that exited the distal end of the dissector and guide attached to a guide member that may be pulled into chest cavity through the thoracotomy by withdrawing the guide wire through the guide wire tube (in direction as indicated by arrow)
Figure 34:
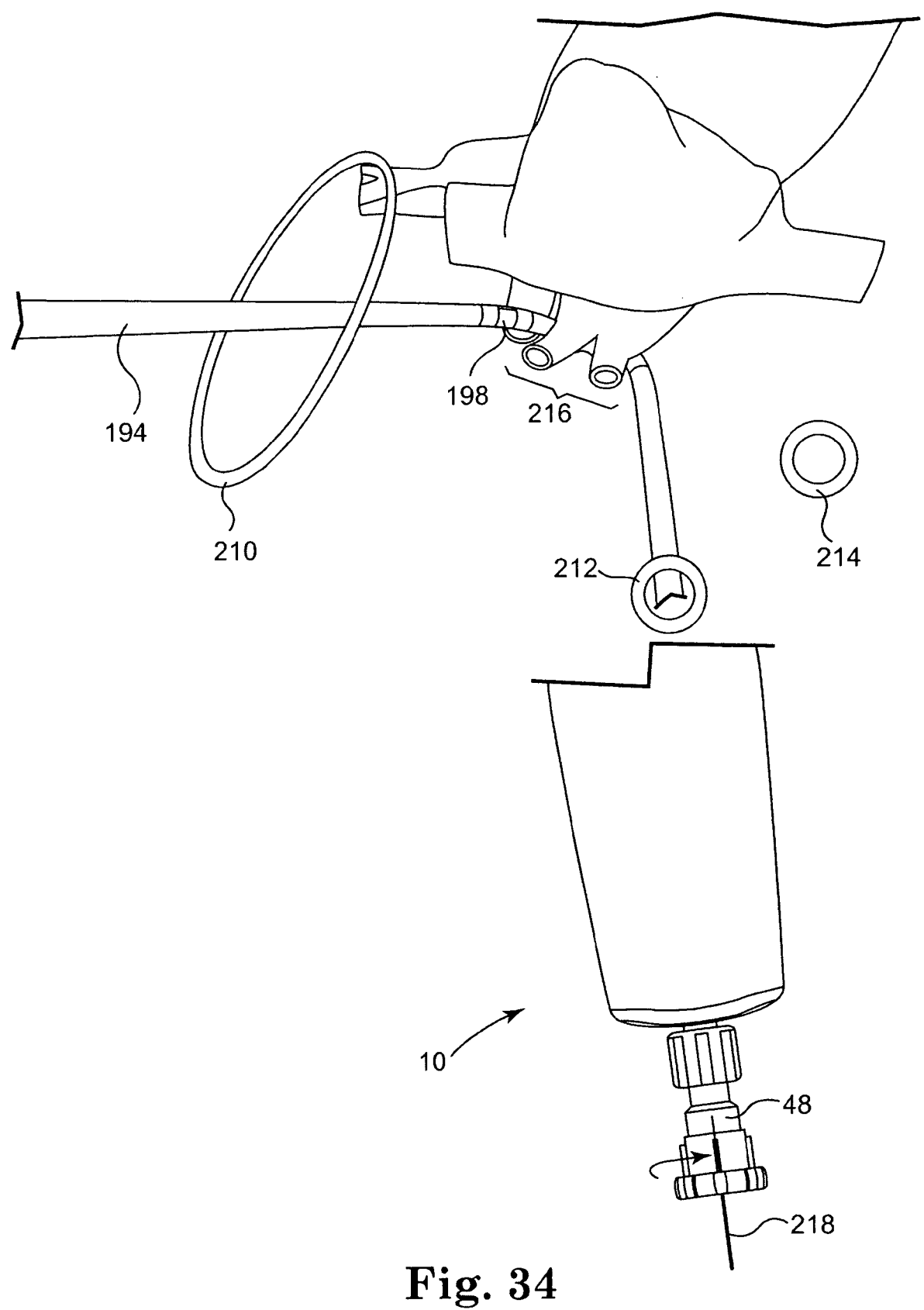
FIG. 34 is an illustration as in FIG. 33, and showing the guide member in contact with the distal tip of the dissector and guide, and also showing locking the guide wire in a guide wire lock (by turning lock as indicated by arrow)

Next, as illustrated in FIG. 33, the guide wire 218 is connected to a guide member 194. The connection between the guide wire 218 and the guide member 194 may be made by inserting the guide wire 218 in the end of the torquer 198 on the guide member 194. The torquer tip 204 may then be twisted, e.g., clockwise, to secure the guide wire 218 in place. The next step, as illustrated in FIG. 33, is to pull the guide wire 218 back out through the dissector 10 in the direction shown by the arrow, which moves the guide member 194 closer to the end of distal tip 30 of the dissector 10. The guide wire 218 is pulled until the torquer 198 of the guide member 194 comes substantially into contact with the distal tip 30 of the dissector 10, as shown by FIG. 34. The next step, also illustrated in FIG. 34, is to lock the guide wire lock 48 by turning (as shown by arrow), e.g., clockwise, the guide wire lock 48.

Figure 35:
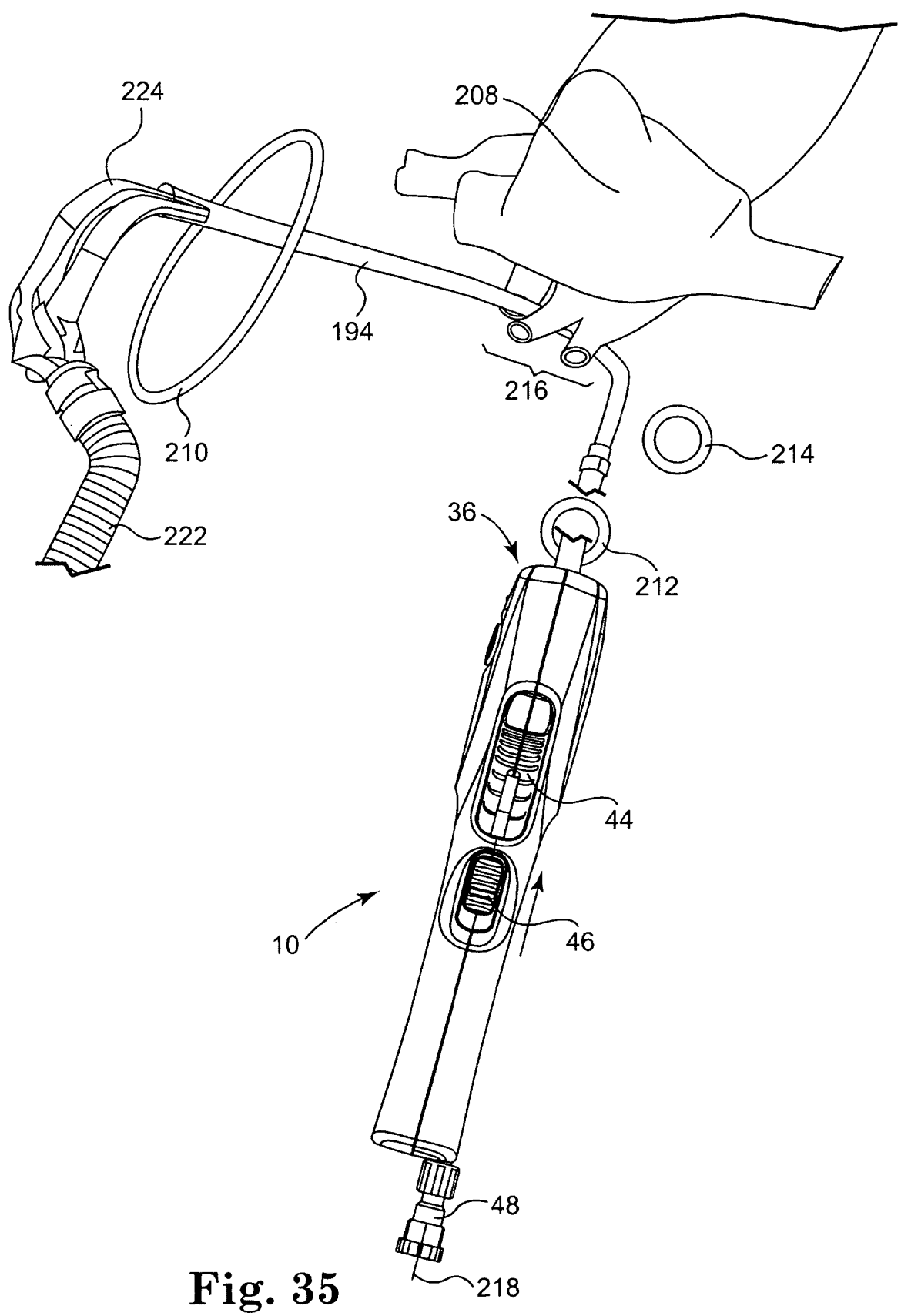
FIG. 35 is an illustration as in FIG. 34, and showing an ablation device attached to the guide member, which may be moved into the chest cavity through the thoracotomy, after the articulation locking mechanism switch (i.e., control wheel lock switch or lock switch) is moved to allow distal portion to straighten as dissector and guide is withdrawn from the port, as a result the ablation device may be pulled into position around the pair of pulmonary veins.
Figure 36:
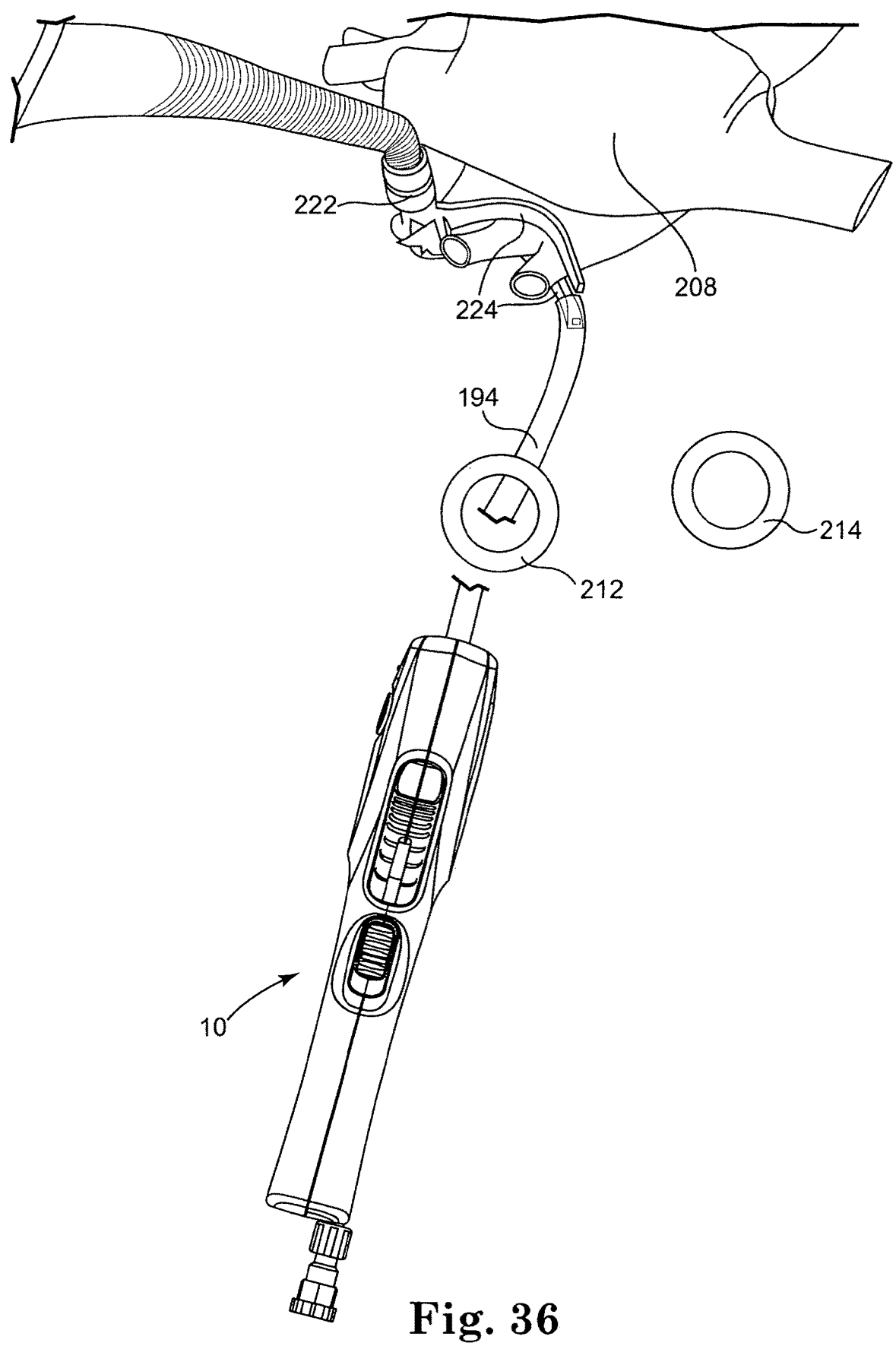
FIG. 36 is an illustration as in FIG. 35, and showing the ablation device in place around the pair of pulmonary veins (with the guide member still attached to the ablation device)

FIG. 35 illustrates a next step in the method, which is to attach an ablation device 222 to the end of the guide member 194 opposite the torquer 198. In order to guide the ablation device 222 into the body to the correct location, the next step in the method is to withdraw the dissector 10 (and guide wire 218) back out through the port of entry 212 and thereby pull the ablation device 222 into place. In order to remove the dissector 10, the distal portion 16 generally needs to be straightened first by unlocking the articulation lock 46 (as shown by arrow) and then by rotating the control wheel 44 toward the distal end 36 of the handle 14 the dissector 10. The dissector 10 is then manually withdrawn from the first port 212. As a result, the attached guide member 194 is pulled through the pericardial reflections and out through the port 212, thereby pulling the attached ablation device 222 to the area of pulmonary veins 216. In order to place the ablation device 222 around the pulmonary veins 216, as shown in FIG. 36, the jaws 224 of the ablation device 222 are closed around the veins 216.

Any known or future developed ablation device is contemplated as being used with the present invention. Such an ablation device may apply any type of suitable energy, such as RF energy, HIFU energy, microwave energy, thermal energy, cryogenic energy, laser energy or ultrasound energy, for examples, to target tissue. A particular, preferred ablation device is a bipolar ablation device, although all types of ablation devices are contemplated.

In other embodiments of the present invention, it is contemplated that the dissector 10 can include components for other purposes besides dissection and guidance. For example, instead of using the dissector 10 to place a separate ablation device, the means for performing ablation (e.g., ablating or energy transfer elements) may be included in the dissector 10. The means for performing ablation or energy transfer can comprise any energy transfer elements that transfer energy to target tissue. For example, energy may be conductive elements that may supply RF energy (as shown in Figs), HIFU energy, microwave energy, thermal energy, cryogenic energy or ultrasound energy to target tissue. Energy transfer elements may be, for example, laser elements for supplying laser light to target tissue. Two or more energy transfer elements or conductive elements may be arranged in a bipolar arrangement wherein at least one element is used as a positive electrode and at least one element is used as a negative electrode. One or more energy transfer elements or conductive elements of the ablation device 12 may be arranged in a monopolar arrangement wherein at least one element is used as one electrode and an indifferent electrode is placed elsewhere on the patient's body such as the back, thigh or shoulder or another site other than the ablation device 12 site.

Energy transfer elements or conductive elements may comprise one or more conductive materials or blends including titanium, titanium alloys, TiNi alloys, shape memory alloys, super elastic alloys, aluminum oxide, platinum, platinum alloys, stainless steels, stainless steel alloys, MP35N, elgiloy, haynes 25, satellite, pyrolytic carbon, silver carbon, conductive metals, conductive polymers or plastics, and/or conductive ceramics. Energy transfer elements or conductive elements may not be conductive but may serve as a conduit to deliver a conductive material such as a conductive fluid. Energy transfer or conductive elements may be porous. For example, energy transfer elements or conductive elements may comprise porous polymers, metals, or ceramics. Energy transfer elements or conductive elements may be coated with non-stick coatings such as PTFE or other types of coatings as discussed herein. In particular, the energy transfer elements may comprise one or more coatings, e.g., hydrophilic coatings. Energy transfer elements or conductive elements may be flexible thereby allowing them to conform to the surface of target tissue. Energy transfer elements or conductive elements may be malleable thereby allowing a surgeon to shape them to conform to the surface of target tissue.

Energy transfer elements or conductive elements may comprise one or more metal conductors such as windings inside a polymer or a conductive mesh material. The energy transfer elements or conductive elements may comprise tubes for delivery of fluids. The tubes may comprise holes or slots. A polymer tube may be placed inside a metal tube to control fluid delivery through energy transfer elements or conductive elements. One or more of the energy transfer elements or conductive elements may be used as one or more nerve stimulation electrodes and/or as one or more cardiac stimulation electrodes. Electrodes may be used for cardiac pacing, defibrillation, cardioversion, sensing, stimulation and/or mapping.

Energy transfer elements or conductive elements may comprise needles designed to penetrate tissues such as fat and muscle. For example, energy transfer elements or conductive elements may be designed to penetrate fat on the heart thereby allowing the energy transfer elements or conductive elements to reach cardiac tissue. The needles may allow fluids such as conductive fluids, chemicals such as ablation chemicals, drugs, biological agents and/or cells to pass through. The needles may allow a vacuum or suction to pass through.

In addition, the dissector 10 may include components for other features besides ablation. For example, the dissector 10 may include means for tracking the position of the device 10 in a body (e.g., tracking the distal portion 16). An example of a disclosure of such a tracking means is described in U.S. Patent Application Publication US 2006/0229594 A1 (Francischelli et al.), and is herein incorporated by reference in its entirety. Alternatively, or additionally, the dissector 10 may include any other desired features. For example, the dissector 10 may include any of the following features: sensing capabilities, imaging capabilities, fluid transfer (e.g., hydration and/or desiccation) capabilities, aeration capabilities, and cutting capabilities (e.g., cutting tool included on distal portion). Other suitable capabilities are also contemplated by the present invention.

The next step in such a method is that the guide member 194 is removed from the ablation device 222. The dissector 10 and guide member 194 are then completely removed from the patient. Ablating energy is then delivered to the ablation device 222 to ablate tissue. Following the ablation procedure, the ablation device 222 is withdrawn or removed from the patient. In the exemplary method illustrated in FIGS. 30-36, the jaws 224 would be removed from the pulmonary veins 216, and the ablation device 222 would be withdrawn back through the thoracotomy 210 and out of the body.

Without reference to any particular figures, in general, the present invention contemplates using the dissector 10 as part of a system for dissecting tissue and/or guiding a medical device to a desired physiological location. The system may comprise: a dissecting/guiding device 10, comprising: an elongate shaft 12 comprising a proximal portion 18 and a distal portion 16, wherein the distal portion 16 comprises a plurality of segments that articulate with respect to one another; a handle 14 attached to the proximal portion 18 of the shaft 12, wherein the handle 14 comprises controls for articulating the plurality of segments of the distal portion 16 of the shaft 12 with respect to one another; and a guide wire tube 68 through at least a portion of the length of the dissecting/guiding device 10, wherein the guide wire tube 68 comprises proximal and distal ends each having an opening; a guide wire that may be fed into the proximal end of the guide wire tube 68, through the guide wire tube 68 and out through the distal opening of the guide wire tube 68; and a guide member 194 comprising an elongate structure with two ends, wherein a first end may attach to a distal end of the guide wire and a second end that may attach to a medical device, such that when the guide wire, with the medical device attached, is retracted back through the guide wire tube 68, the medical device is guided to a desired physiological location.

FIGS. 30-36, discussed above, demonstrate using the dissector 10 to dissect pericardial reflection tissue and to place an ablation device to treat atrial fibrillation. However, the present invention also contemplates using the dissector 10 more broadly during other surgical procedures performed to treat other conditions. Therefore, more broadly, the present invention includes a method of surgical dissection of tissue with a dissector 10 comprising: an elongate shaft 12 comprising a proximal portion 18 and a distal portion 16, wherein the distal portion 16 comprises a plurality of segments that articulate with respect to one another and the plurality of segments includes a distal segment 20 having a distal end; and a handle 14 attached to the proximal portion 18 of the shaft 12, wherein the handle 14 comprises controls for articulating the plurality of segments of the distal portion 16 of the shaft 12 with respect to one another, comprising the steps of: positioning the distal end of the dissector 10 in a body; advancing the distal end through the body to dissect tissue; and simultaneously articulating the plurality of segments with respect to one another. The distal end may include an illumination source 32, and the method may further comprise the step of visually locating the distal portion 16 of the elongate shaft 12 by observing visible energy from the illumination source 32 passing through tissue, or may further comprise the step of differentiating tissue by observing visible energy from the illumination source 32 through tissue.

The present invention also includes a method of guiding a second device to a desired physiological location with a first device comprising: an elongate shaft 12 comprising a proximal portion 18 and a distal portion 16, wherein the distal portion 16 comprises a plurality of segments that articulate with respect to one another and the plurality of segments includes a distal segment 20 having a distal end; a handle 14 attached to the proximal portion 18 of the shaft 12, wherein the handle 14 comprises controls for articulating the plurality of segments of the distal portion 16 of the shaft 12 with respect to one another; and a guide wire tube 68 having a proximal and a distal end, wherein the guide wire tube 68 is disposed along at least a portion of the length of the first device and the guide wire tube 68 has openings at both the proximal and distal ends, comprising the steps of: inserting the first device, distal end first, into a first opening in a body with the plurality of segments of the distal portion in a substantially straight configuration; advancing the distal end through the body; articulating the plurality of segments with respect to one another to position the distal portion in a desired physiological location; feeding a guide wire, having a proximal and a distal end, into the proximal opening of the guide wire tube, distal end first, and through the guide wire tube until the distal end of the guide wire comes out the distal opening of the guide wire tube in the distal end of the first device; connecting the second device to the distal end of the guide wire; and pulling the guide wire back through the first device and thereby pulling the second device adjacent the distal end of the first device at or near a desired physiological location. The method may further comprise the step of removing the first device through the first opening. Prior to the step of removing the first device, the distal portion of the first device may be returned to the substantially straight configuration. The method of guiding may further comprise the steps of: disconnecting the second device from the guide wire; and removing the first device and the guide wire through the first opening. The second device in the method may be inserted into the body through a second opening in order to connect the second device to the guide wire. If the distal end includes an illumination source 32, the method may further comprise the step of visually locating the distal end of the elongate shaft 12 by observing visible energy from the illumination source 32 passing through tissue. The illumination source 32 may be turned off and on. If the first device further comprises an articulation lock mechanism for maintaining the distal portion 16 of the device in a desired articulated configuration, the method may further comprise the step of locking the distal portion 16 in the articulated position while the distal portion 16 is in the desired physiological location. Additionally, with the presence of an articulation lock mechanism (i.e., control wheel lock), lock could be unlocked to allow the distal portion 16 of the first device to be returned to the substantially straight configuration, particularly prior to removal from through the first opening. If the first device further comprises a guide wire lock that can maintain the position of the guide wire in the guide wire tube 68, the method may further comprise the step of locking the guide wire in a position in the guide wire tube 68 after the step of pulling the guide wire back through the first device.

A method combining the steps of dissection and guiding of a second device is also contemplated by the present invention.

The dissector 10 and its components, as well as the other parts of the system disclosed, are preferably made of biocompatible materials such as stainless steel, biocompatible epoxy or biocompatible plastic. Preferably, a biocompatible material prompts little allergenic response from the patient's body and is resistant to corrosion from being placed within the patient's body. Furthermore the biocompatible material preferably does not cause any additional stress to the patient's body, for example, it does not scrape detrimentally against any element within the surgical cavity.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A surgical dissector comprising:
   an elongate shaft including a proximal portion and a distal portion, wherein the distal portion comprises a plurality of hingedly interconnected segments that articulate with respect to one another and the plurality of segments includes a distal segment having a distal end; and
   a handle attached to the proximal portion of the shaft, wherein the handle comprises controls for articulating the plurality of segments of the distal portion of the shaft with respect to one another; wherein each of the plurality of segments are hingedly interconnected with a respective pin that extends laterally through adjacent segments; and
   a push/pull rod interconnected to a plurality of connected pistons serially and hingedly interconnected adjacent the plurality of segments; wherein the entirety of the push/pull rod is positioned proximal the plurality of pistons and the plurality of pistons are positioned distal to the push/pull rod.

2. The surgical dissector of claim 1, wherein the distal end includes an illumination source.

3. The surgical dissector of claim 1, wherein the plurality of pistons are serially and hingedly interconnected with a plurality of links.

4. The surgical dissector of claim 3, wherein each link includes two holes in which respective pins are received.

5. The surgical dissector of claim 1, wherein, in a straight configuration, the plurality of segments and the plurality of pistons are parallel and adjacent with respect to each other.

6. The surgical dissector of claim 1, wherein a proximal end of the push/pull rod is pivotally connected to the distal segment.

7. The surgical dissector of claim 1, further comprising a flexible guide wire tube extending lengthwise along the elongate shaft.

8. The surgical dissector of claim 7, wherein the guide wire tube extends adjacent an illumination source.

9. The surgical dissector of claim 1, further comprising a handle that controls movement of the push/pull rod.

10. The surgical dissector of claim 9, further comprising a rack extending from the push/pull rod, the rack including a set of teeth.

11. The surgical dissector of claim 10, wherein the handle includes a set of teeth that engage the set of teeth of the rack.

12. The surgical dissector of claim 11, further comprising a jam bar connected to the rack.

13. The surgical dissector of claim 12, further comprising a guide wire tube supporting a jam plate having an aperture aligned with the jam bar.

14. The surgical dissector of claim 1, further comprising an articulation lock mechanism for maintaining the distal portion of shaft in a desired articulated configuration.

* * * * *